(12) United States Patent
West et al.

(10) Patent No.: US 12,289,413 B2
(45) Date of Patent: Apr. 29, 2025

(54) BIOMETRIC IDENTIFICATION SYSTEMS AND ASSOCIATED DEVICES

(71) Applicant: Tesseract Health, Inc., Guilford, CT (US)

(72) Inventors: Lawrence C. West, San Jose, CA (US); Maurizio Arienzo, New York, NY (US); Owen Kaye-Kauderer, Brooklyn, NY (US); Tyler S. Ralston, Clinton, CT (US); Benjamin Rosenbluth, New Haven, CT (US); Jonathan M. Rothberg, Miami Beach, FL (US); Jacob Coumans, Old Lyme, CT (US); Christopher Thomas McNulty, Guilford, CT (US)

(73) Assignee: Tesseract Health, Inc., Guilford, CT (US)

( * ) Notice: Subject to any disclaimer, the term of this patent is extended or adjusted under 35 U.S.C. 154(b) by 872 days.

(21) Appl. No.: 16/712,822

(22) Filed: Dec. 12, 2019

(65) Prior Publication Data

US 2020/0193004 A1    Jun. 18, 2020

Related U.S. Application Data

(60) Provisional application No. 62/833,179, filed on Apr. 12, 2019, provisional application No. 62/833,210, (Continued)

(51) Int. Cl.
*H04L 9/32* (2006.01)
*A61B 3/10* (2006.01)
(Continued)

(52) U.S. Cl.
CPC ............ *H04L 9/3231* (2013.01); *A61B 3/102* (2013.01); *A61B 3/1208* (2013.01);
(Continued)

(58) Field of Classification Search
CPC ..... H04L 9/3231; H04L 63/0861; A61B 3/10; A61B 3/1208; A61B 5/0066;
(Continued)

(56) References Cited

U.S. PATENT DOCUMENTS

| 4,762,701 A | 8/1988 | Horan et al. |
| 5,973,731 A | 10/1999 | Schwab |

(Continued)

FOREIGN PATENT DOCUMENTS

| EP | 3561795 A1 * 10/2019 | ............. G06F 3/011 |
| JP | 2003085662 A * 3/2003 | |

(Continued)

OTHER PUBLICATIONS

Invitation to Pay Additional Fees for International Application No. PCT/US2019/066062 dated Feb. 13, 2020.

(Continued)

*Primary Examiner* — Mohammed A Hasan
(74) *Attorney, Agent, or Firm* — Wolf, Greenfield & Sacks, P.C.

(57) ABSTRACT

The present disclosure provides techniques and apparatus for capturing an image of a person's retina fundus, identifying the person, accessing various electronic records (including health records) or accounts or devices associated with the person, determining the person's predisposition to certain diseases, and/or diagnosing health issues of the person. Some embodiments provide imaging apparatus having one or more imaging devices for capturing one or more images of a person's eye(s). Imaging apparatus described herein may include electronics for analyzing and/or exchanging captured image and/or health data with other devices. In accordance with various embodiments, imaging apparatus described herein may be alternatively or addition- (Continued)

ally configured for biometric identification and/or health status determination techniques, as described herein.

14 Claims, 25 Drawing Sheets

Related U.S. Application Data filed on Apr. 12, 2019, provisional application No. 62/833,239, filed on Apr. 12, 2019, provisional application No. 62/778,494, filed on Dec. 12, 2018.

(51) Int. Cl.

| | | |
|---|---|---|
| *A61B 3/12* | (2006.01) | |
| *A61B 5/00* | (2006.01) | |
| *F16M 11/10* | (2006.01) | |
| *G01B 9/02091* | (2022.01) | |
| *G01N 21/17* | (2006.01) | |
| *G06F 18/22* | (2023.01) | |
| *G06F 21/32* | (2013.01) | |
| *G06N 7/01* | (2023.01) | |
| *G06N 20/00* | (2019.01) | |
| *G06T 7/00* | (2017.01) | |
| *G06V 10/82* | (2022.01) | |
| *G06V 30/24* | (2022.01) | |
| *G06V 40/18* | (2022.01) | |
| *G06V 40/19* | (2022.01) | |
| *G06V 40/50* | (2022.01) | |
| *G16H 10/60* | (2018.01) | |
| *G16H 15/00* | (2018.01) | |
| *G16H 30/40* | (2018.01) | |
| *H02J 50/10* | (2016.01) | |
| *G06F 21/62* | (2013.01) | |
| *G06N 3/044* | (2023.01) | |
| *G06N 3/045* | (2023.01) | |

(52) U.S. Cl.
CPC .......... *A61B 5/0066* (2013.01); *F16M 11/10* (2013.01); *G01B 9/02091* (2013.01); *G01N 21/17* (2013.01); *G06F 18/22* (2023.01); *G06F 21/32* (2013.01); *G06N 7/01* (2023.01); *G06N 20/00* (2019.01); *G06T 7/0012* (2013.01); *G06T 7/0014* (2013.01); *G06V 10/82* (2022.01); *G06V 30/248* (2022.01); *G06V 40/19* (2022.01); *G06V 40/193* (2022.01); *G06V 40/197* (2022.01); *G06V 40/50* (2022.01); *G16H 10/60* (2018.01); *G16H 15/00* (2018.01); *G16H 30/40* (2018.01); *H02J 50/10* (2016.02); *G01N 2021/1787* (2013.01); *G06F 21/6245* (2013.01); *G06N 3/044* (2023.01); *G06N 3/045* (2023.01); *G06T 2207/20081* (2013.01); *G06T 2207/20084* (2013.01); *G06T 2207/30041* (2013.01)

(58) Field of Classification Search
CPC ... A61B 3/0025; A61B 3/1241; A61B 5/0022; A61B 5/0071; A61B 5/117; A61B 3/1225; A61B 5/7264; F16M 11/10; G01B 9/02091; G01B 9/0203; G01N 21/17; G01N 2021/1787; G06F 18/22; G06F 21/32; G06F 21/6245; G06N 7/01; G06N 20/00; G06N 3/044; G06N 3/045; G06N 3/084; G06T 7/0012; G06T 7/0014; G06T 2207/20081; G06T 2207/20084; G06T 2207/30041; G06T 2207/10101; G06V 10/82; G06V 30/248; G06V 40/19; G06V 40/193; G06V 40/197; G06V 40/50; G06V 40/10; G16H 10/60; G16H 15/00; G16H 30/40; G16H 50/20; G16H 50/70; H02J 50/10
See application file for complete search history.

(56) References Cited

U.S. PATENT DOCUMENTS

| | | | |
|---|---|---|---|
| 6,082,859 | A | 7/2000 | Okashita et al. |
| 6,142,629 | A * | 11/2000 | Adel ............... G01J 3/2823 351/206 |
| 7,555,148 | B1 | 6/2009 | Steinberg et al. |
| 8,184,867 | B2 | 5/2012 | Otto et al. |
| 8,503,749 | B2 | 8/2013 | Tobin et al. |
| 9,710,016 | B1 * | 7/2017 | Porzio ............... G06F 1/1632 |
| 9,808,154 | B2 | 11/2017 | Cleland et al. |
| 10,653,311 | B1 | 5/2020 | Pascal et al. |
| 2002/0052551 | A1 | 5/2002 | Sinclair et al. |
| 2003/0198368 | A1 | 10/2003 | Kee |
| 2004/0008321 | A1 | 1/2004 | Saigusa et al. |
| 2006/0244913 | A1 | 11/2006 | Gellermann et al. |
| 2008/0212847 | A1 * | 9/2008 | Davies ............... G16H 10/40 382/116 |
| 2009/0147217 | A1 | 6/2009 | Molnar et al. |
| 2010/0183199 | A1 | 7/2010 | Smith et al. |
| 2010/0309303 | A1 | 12/2010 | Sanchez Ramos et al. |
| 2011/0282331 | A1 | 11/2011 | Brennan et al. |
| 2012/0092619 | A1 | 4/2012 | Rowe |
| 2014/0125949 | A1 * | 5/2014 | Shea ............... A61B 3/103 351/205 |
| 2015/0157505 | A1 | 6/2015 | Neev |
| 2015/0265172 | A1 | 9/2015 | Fuller et al. |
| 2015/0288687 | A1 * | 10/2015 | Heshmati ............ H04L 67/10 726/7 |
| 2016/0143523 | A1 | 5/2016 | Miyashita et al. |
| 2016/0296112 | A1 | 10/2016 | Fletcher et al. |
| 2016/0320837 | A1 | 11/2016 | Swedish et al. |
| 2016/0335512 | A1 | 11/2016 | Bradski |
| 2017/0007843 | A1 | 1/2017 | Samec et al. |
| 2017/0079522 | A1 | 3/2017 | Artsyukhovich et al. |
| 2018/0018451 | A1 | 1/2018 | Spizhevoy et al. |
| 2018/0028691 | A1 | 2/2018 | Feuerstein et al. |
| 2018/0140180 | A1 | 5/2018 | Coleman |
| 2018/0235467 | A1 | 8/2018 | Celenk et al. |
| 2018/0253539 | A1 | 9/2018 | Minter et al. |
| 2018/0280196 | A1 | 10/2018 | Luttrull et al. |
| 2018/0315193 | A1 * | 11/2018 | Paschalakis ......... G06V 40/197 |
| 2018/0320145 | A1 | 11/2018 | Chalberg et al. |
| 2018/0330162 | A1 * | 11/2018 | Hanna ................. G06T 7/20 |
| 2019/0206054 | A1 | 7/2019 | Mao et al. |
| 2019/0261853 | A1 | 8/2019 | Williamson |
| 2020/0100673 | A1 * | 4/2020 | Shimizu ............... A61B 3/14 |
| 2020/0125829 | A1 | 4/2020 | Cox et al. |
| 2020/0193156 | A1 | 6/2020 | Ralston et al. |
| 2020/0193592 | A1 * | 6/2020 | Arienzo ............... G16H 50/20 |
| 2020/0397287 | A1 | 12/2020 | Ralston et al. |
| 2021/0127969 | A1 | 5/2021 | Oggenfuss et al. |

FOREIGN PATENT DOCUMENTS

| | | |
|---|---|---|
| JP | 2008-005987 A | 1/2008 |
| JP | 4527471 B2 | 8/2010 |
| RU | 2611202 C2 | 2/2017 |
| WO | WO 2015/188142 A1 | 12/2015 |
| WO | WO 2017/030770 A1 | 2/2017 |
| WO | WO 2018/112254 A1 | 6/2018 |
| WO | WO 2018/213492 A1 | 11/2018 |

OTHER PUBLICATIONS

Invitation to Pay Additional Fees for International Application No. PCT/US2019/066067 dated Feb. 12, 2020.
Invitation to Pay Additional Fees for International Application No. PCT/US2019/066069 dated Feb. 13, 2020.

(56) References Cited

OTHER PUBLICATIONS

Invitation to Pay Additional Fees for International Application No. PCT/US2019/066073 dated Feb. 14, 2020.
[No Author Listed], Optomap af Diagnostic Atlas. A Retinal Reference Guide. Optos Building The Retina Company. 2016. 37 pages.
Fukuta et al., Personal Identification Based on Blood Vessels of Retinal Fundus Images. Proc of SPIE. 2008;6914:69141V. 9 pages, doi: 10.1117/12.769330.
Lahiri et al., Retinal Vessel Segmentation under Extreme Low Annotation: A Generative Adversarial Network Approach. arXiv:1809.01348v1. Sep. 5, 2018. 9 pages.
Mazumdar et al., Retina Based Biometric Authentication System: A Review. International Journal of Advanced Research in Computer Science. 2018;9(1):711-718. DOI:http://dx.doi.org/10.26483/ijarcs.v9i1.5322.
Son et al., Retinal Vessel Segmentation in Fundoscopic Images with Generative Adversarial Networks. arXiv:1706.09318v1. Jun. 28, 2017. 9 pages.
International Search Report and Written Opinion for International Application No. PCT/US2019/066062 dated Apr. 8, 2020.
International Search Report and Written Opinion for International Application No. PCT/US2019/066067 dated Apr. 8, 2020.
International Search Report and Written Opinion for International Application No. PCT/US2019/066069 dated Apr. 24, 2020.
International Search Report and Written Opinion for International Application No. PCT/US2019/066073 dated Apr. 28, 2020.
U.S. Appl. No. 16/907,102, filed Jun. 19, 2020, Ralston et al.
International Preliminary Report on Patentability for International Application No. PCT/US2019/066062 dated Jun. 24, 2021.
International Preliminary Report on Patentability for International Application No. PCT/US2019/066069 dated Jun. 24, 2021.
International Preliminary Report on Patentability for International Application No. PCT/US2019/066073 dated Jun. 24, 2021.
Karen, The Most Comfortable iPhone Armband Ever. Easy DIY. The Art of Doing Stuff. Jun. 28, 2018. 5 pages.
Yao et al., Convolutional Neural Networks for Retinal Blood Vessel Segmentation. 2016 9th International Symposium on Computational Intelligence and Design. IEEE. pp 406-409. doi: 10.1109/ISCID.2016.99.
Invitation to Pay Additional Fees for International Application No. PCT/US2020/038817, dated Sep. 15, 2020.
International Search Report and Written Opinion for International Application No. PCT/US2020/038817, dated Nov. 10, 2020.
U.S. Appl. No. 16/712,831, filed Dec. 12, 2019, Rothberg et al.
U.S. Appl. No. 16/712,843, filed Dec. 12, 2019, Ralston et al.
U.S. Appl. No. 16/712,854, filed Dec. 12, 2019, Arienzo et al.
International Preliminary Report on Patentability dated Dec. 30, 2021, in connection with International Application No. PCT/US2020/038817.
Extended European Search Report dated Aug. 18, 2022, in connection with European Application No. 19894646.9.
Fritzsche, Computer vision algorithms for retinal vessel width change detection and quantification. Rensselaer Polytechnic Institute. Oct. 2002. 50 pages.
Hung et al., An Enhanced security for government base on multi-factor biometric authentication. International Journal of Computer Networks & Communications (IJCNC). 2016;8(6):55-72.
Extended European Search Report dated Sep. 16, 2022, in connection with European Application No. 19897370.3.
Extended European Search Report dated Oct. 10, 2022, in connection with European Application No. 19896670.7.
Duncan, Phenylketonuria (PKU) Cards: An underutilized resource in forensic investigations. Emerging and Advanced Technologies in Diverse Forensic Sciences. Sep. 2019. 15 pages.
Supplementary European Search Report dated Oct. 5, 2022, in connection with European Application No. 198973703.3.
Dysli et al., Fluorescence lifetime imaging ophthalmoscopy. Elsevier. Sep. 2017;60:120-143.
Pretty et al., (Quantitative Light Fluorescence (QLF) and Polarized White Light (PWL) assessments of dental fluorosis in an epidemiological setting. BMC Public Health. 2012.12:366. 10 pages.

\* cited by examiner

FIG. 5A-C

BIOMETRIC IDENTIFICATION SYSTEMS AND ASSOCIATED DEVICES

CROSS REFERENCE TO RELATED APPLICATIONS

This application claims priority under 35 U.S.C. 119(e) to: U.S. Provisional Application Ser. No. 62/833,179, filed Apr. 12, 2019, and entitled "BIOMETRIC IDENTIFICATION SYSTEMS AND ASSOCIATED DEVICES"; U.S. Provisional Application Ser. No. 62/833,210, filed Apr. 12, 2019, entitled "BIOMETRIC IDENTIFICATION TECHNIQUES"; U.S. Provisional Application Ser. No. 62/833,239, filed Apr. 12, 2019, and entitled "BIOMETRIC IDENTIFICATION AND HEALTH STATUS DETERMINATION"; and U.S. Provisional Application Ser. No. 62/778,494, filed Dec. 12, 2018, and entitled "RETINAL IMAGING", each application of which is herein incorporated by reference in its entirety.

FIELD OF THE DISCLOSURE

The present application relates to biometric identification, such as using a person's retina fundus.

BACKGROUND

Present techniques for identifying a person, accessing a person's private devices or accounts, determining a health status of a person, and/or diagnosing a health condition of the person would benefit from improvement.

BRIEF SUMMARY

Some aspects of the present disclosure provide a system comprising an imaging and/or measurement apparatus configured to capture a first image and/or measurement of a person's retina fundus, a first processor configured to transmit, over a communication network, first image and/or measurement data associated with and/or including the first image and/or measurement, and a second processor configured to receive, over the communication network, the first image and/or measurement data, and identify the person based on the first image and/or measurement data.

Some aspects of the present disclosure provide a device configured to transmit, over a communication network, first image and/or measurement data associated with and/or including a first image and/or measurement of a person's retina fundus, and receive, over the communication network, an identity of the person.

Some aspects of the present disclosure provide a method comprising transmitting, over a communication network, first image and/or measurement data associated with and/or including a first image and/or measurement of a person's retina fundus, and receiving, over the communication network, an identity of the person.

Some aspects of the present disclosure provide a device configured to update health information associated with a person based on first image and/or measurement data associated with and/or including a first image and/or measurement of the person's retina fundus.

Some aspects of the present disclosure provide a method comprising updating health information associated with a person based on first image and/or measurement data associated with and/or including a first image and/or measurement of the person's retina fundus.

Some aspects of the present disclosure provide a system comprising at least one processor configured to, based on first image and/or measurement data associated with and/or including a first image and/or measurement of a person's retina fundus, access health information of the person.

Some aspects of the present disclosure provide a device configured to, based on first image and/or measurement data associated with and/or including a first image and/or measurement of a person's retina fundus, access health information of the person.

Some aspects of the present disclosure provide a method comprising, based on first image and/or measurement data associated with and/or including a first image and/or measurement of a person's retina fundus, accessing heath information of the person.

Some aspects of the present disclosure provide a system comprising at least one processor configured to, based on first image and/or measurement data associated with and/or including a first image and/or measurement of a person's retina fundus, access a first user domain for operating a device.

Some aspects of the present disclosure provide a device configured to, based on first image and/or measurement data associated with and/or including a first image and/or measurement of a person's retina fundus, access a first user domain for operating the device.

Some aspects of the present disclosure provide a method comprising, based on first image and/or measurement data associated with and/or including a first image and/or measurement of a person's retina fundus, accessing a first user domain for operating a device.

The foregoing summary is not intended to be limiting. In addition, various embodiments may include any aspects either alone or in combination.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1:
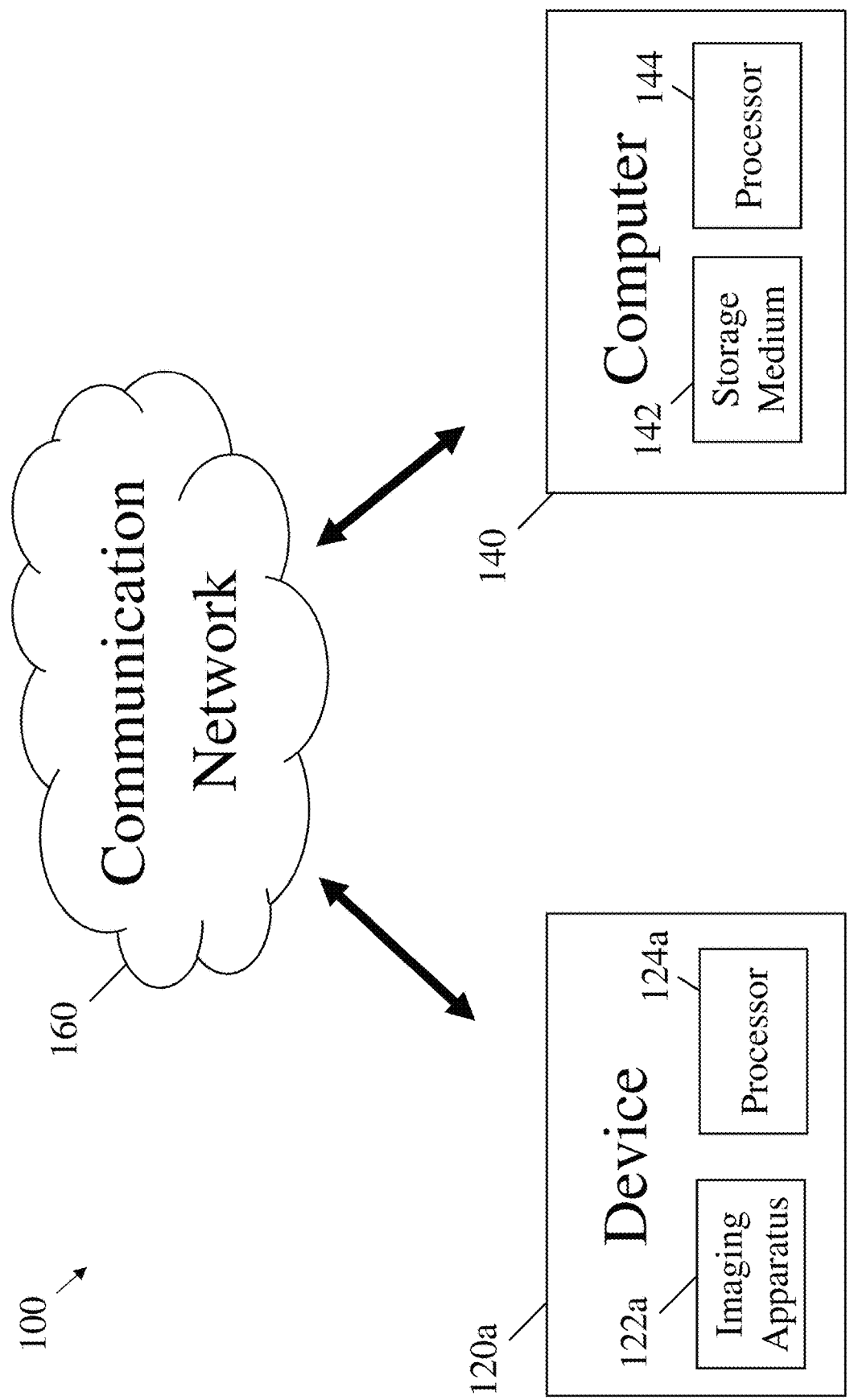
FIG. 1 is a block diagram of a cloud-connected system for biometric identification and health or other account access, in accordance with some embodiments of the technology described herein.

The inventors have discovered that a captured image of a person's retina fundus can be used to identify a person, determine the person's predisposition to certain diseases, and/or diagnose health issues of the person. Accordingly, the inventors have developed techniques for capturing an image of a person's retina fundus. Further, the inventors have developed techniques for identifying a person, accessing various electronic records (including health records) or accounts or devices associated with the person, determining the person's predisposition to certain diseases, and/or diagnosing health issues of the person.

Some embodiments of the technology described herein provide systems for cloud-based biometric identification capable of protecting sensitive data such as electronic records or accounts stored on the cloud. Some embodiments provide systems for storing health information associated with various patients on the cloud, and/or for protecting patients' health information with a biometric identification system such that the health information may be more accessible to patients without sacrificing security or confidentiality. In some embodiments, a biometric identification system may be integrated together with a system for storing health information and/or for determining a medical condition of the patients, such that data from one or more captured image(s) used to identify a person may also be used to update the person's health information, and/or to determine a medical condition of the person.

The inventors have recognized several problems in current security systems such as for authentication using alphanumeric password or passcode systems and various forms of biometric security. Alphanumeric password or passcode systems may be susceptible to hacking, for example by brute force (e.g., attempting every possible alphanumeric combination). In such cases, users may strengthen their passwords by using a long sequence of characters or by using a greater diversity of characters (such as punctuation or a mix of letters and numbers). However, in such methods, passwords are more difficult for users to remember. In other cases, users may select passwords or passcodes which incorporate personal information (e.g., birth dates, anniversary dates, or pet names), which may be easier to remember but also may be easier for a third party to guess.

While some biometric security systems are configured for authentication such as by voiceprint, face, fingerprint, and iris identification may provide improved fraud protection compared to password and passcode systems, the inventors have recognized that these systems end up being inefficient at identifying the correct person. Typically, these systems will either have a high false acceptance rate or a false rejection rate. A high false acceptance rate makes fraudulent activity easier, and a high false rejection rate makes it more difficult to positively identify the patient. In addition, while other systems such as DNA identification are effective at identifying the correct person, the inventors have recognized that such systems are overly invasive. For example, DNA identification requires an invasive testing procedure such as a blood or saliva sample, which becomes increasingly impractical and expensive as identification is done with increasing frequency. Further, DNA identification is expensive and may be susceptible to fraud by stealing an artifact such as a hair containing DNA.

To solve the problems associated with existing systems, the inventors have developed biometric identification systems configured to identify a person using a captured image of the person's retina fundus. Such systems provide a minimally invasive imaging method with a low false acceptance rate and a low false rejection rate.

Moreover, biometric identification as described herein is further distinguished from authentication techniques of conventional systems in that biometric identification systems described herein may be configured to not only confirm the person's identity but actually to determine the person's identity without needing any information from the person. Authentication typically requires that the person provide identification information along with a password, passcode, or biometric measure to determine whether the identification information given matches the password, passcode, or biometric measure. In contrast, systems described herein may be configured to determine the identity of a person based on one or more captured images of the person's retina fundus. In some embodiments, further security methods such as a password, passcode, or biometric measure such as voiceprint, face, fingerprint, and iris of the person may be obtained for further authentication to supplement the biometric identification. In some embodiments, a person may provide identification information to a biometric identification system in addition to the captured image(s) of the person's retina fundus.

The inventors have further recognized that retina fundus features which may be used to identify a person from a captured image may also be used as indicators of the person's predisposition to certain diseases, and even to diagnose a medical condition of the person. Accordingly, systems described herein may be alternatively or additionally configured to determine the person's predisposition to various diseases, and to diagnose some health issues of the person. For example, upon capturing or otherwise obtaining one or more images of the person's retina fundus for identification, the system may also make such determinations or diagnoses based on the image(s).

Figure 2:
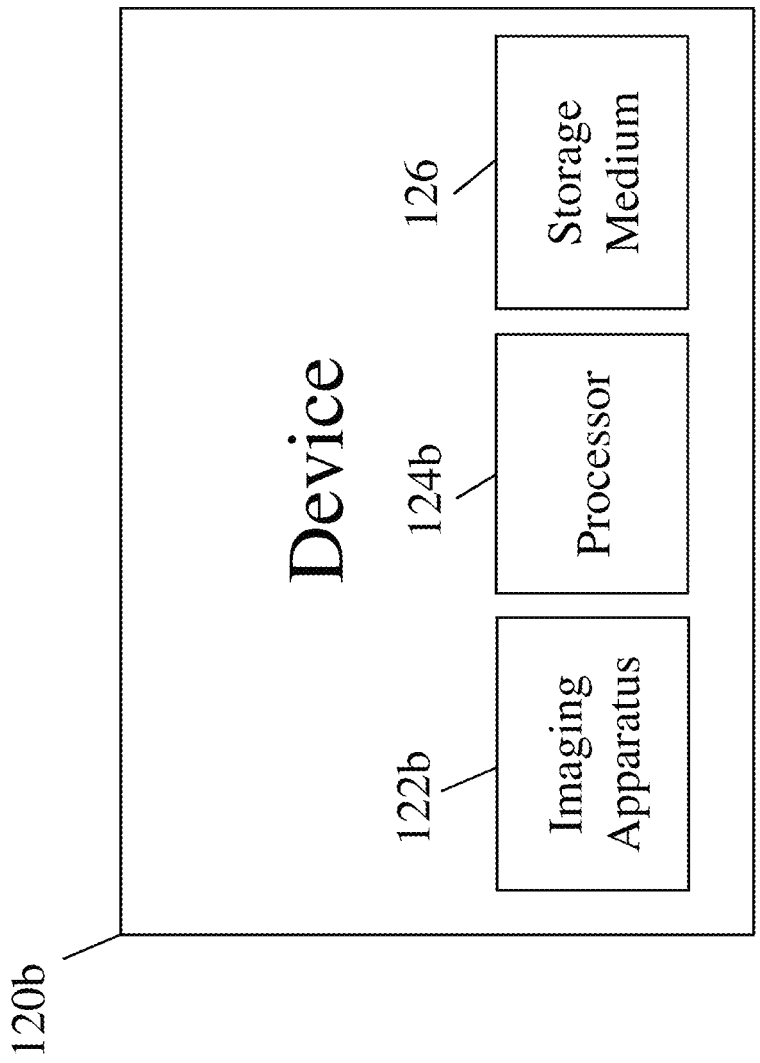
FIG. 2 is a block diagram an exemplary device for local biometric identification and health or other account access, in accordance with some embodiments of the system illustrated in FIG. 1.

Turning to the figures, FIGS. 1-2 illustrate exemplary systems and devices configured to implement techniques for any or each of biometric identification, health information management, medical condition determination, and/or electronic account access. The description of these techniques which follows the description of the systems and devices will refer back to the systems and devices illustrated in FIGS. 1-2.

Referring to FIGS. 1-2, FIG. 1 illustrates a cloud-connected system in which a device may communicate with a remote computer to perform various operations associated with the techniques described herein. In contrast to FIG. 1, FIG. 2 illustrates a device which may be configured to perform any or all of the techniques described herein locally on the device.

With reference to FIG. 1, the inventors have recognized that the processing required for biometric identification, health information management, and other tasks on a user-end device may require, at least in some circumstances, power-hungry and/or expensive processing and/or memory components. To solve these problems, the inventors have developed cloud-connected systems and devices which may offset some or all of the most demanding processing and/or memory intensive tasks onto a remote computer, such that user-end devices may be implemented having less expensive and more power efficient hardware. In some instances, the device may only need to capture an image of a person and transmit data associated with the image to the remote computer. In such instances, the computer may perform biometric identification, access/update health information and/or account information, and/or determine a medical condition based on the image data, and transmit the resulting data back to the device. Because the device may only capture an image and transmit data associated with the image to the computer, the device may require very little processing power and/or memory, which facilitates a corresponding decrease in both cost and power consumption at the device end. Thus, the device may have an increased battery life and may be more affordable to the end user.

FIG. 1 is a block diagram of exemplary system 100 including device 120a and computer 140, which are connected to communication network 160.

Device 120a includes imaging apparatus 122a and processor 124a. In some embodiments, device 120a may be a portable device such as a mobile phone, a tablet computer, and/or a wearable device such as a smart watch. In some embodiments, device 120a may include a standalone network controller for communicating over communication network 160. Alternatively, the network controller may be integrated with processor 124a. In some embodiments, device 120a may include one or more displays for providing information via a user interface. In some embodiments, imaging apparatus 122a may be packaged separately from other components of device 120a. For example, imaging apparatus 122a may be communicatively coupled to the other components, such as via an electrical cable (e.g., universal serial bus (USB) cable) and/or a wired or wireless network connection. In other embodiments, imaging apparatus 122a may be packaged together with other components of device 120a, such as within a same mobile phone or tablet computer housing, as examples.

Computer 140 includes storage medium 142 and processor 144. Storage medium 142 may contain images and/or data associated with images for identifying a person. For example, in some embodiments, storage medium 142 may contain retina fundus images and/or data associated with retina fundus images for comparing to retina fundus images of the person to be identified.

In accordance with various embodiments, communication network 160 may be a local area network (LAN), a cell phone network, a Bluetooth network, the internet, or any other such network. For example, computer 140 may be positioned in a remote location relative to device 120*a*, such as a separate room from device 120*a*, and communication network 160 may be a LAN. In some embodiments, computer 140 may be located in a different geographical region from device 120*a*, and may communicate over the internet.

It should be appreciated that, in accordance with various embodiments, multiple devices may be included in place of or in addition to device 120*a*. For example, an intermediary device may be included in system 100 for communicating between device 120*a* and computer 140. Alternatively or additionally, multiple computers may be included in place of or in addition to computer 140 to perform various tasks herein attributed to computer 140.

FIG. 2 is a block diagram of exemplary device 120*b*, in accordance with some embodiments of the technology described herein. Similar to device 120*a*, device 120*b* includes imaging apparatus 122*b* and processor 124*b*, which may be configured in the manner described for device 120*a*. Device 120*b* may include one or more displays for providing information via a user interface. Device 120*b* also includes storage medium 126. Data stored on storage medium 126, such as image data, health information, account information, or other such data may facilitate local identification, health information management, medical condition determination, and/or account access on device 120*b*. It should be appreciated that device 120*b* may be configured to perform any or all operations associated with the techniques described herein locally, and in some embodiments may transmit data to a remote computer such as computer 140 so as to perform such operations remotely. For example, device 120*b* may be configured to connect to communication network 160.

I. Techniques and Apparatus for Obtaining an Image of and/or Measuring a Person's Retina The inventors have developed techniques for capturing one or more images of a person's retina fundus and/or obtaining data associated with the images, aspects of which are described with reference to FIGS. 1-2.

Imaging apparatus 122*a* or 122*b* may be configured to capture a single image of the person's retina fundus. Alternatively, imaging apparatus 122*a* or 122*b* may be configured to capture multiple images of the person's retina fundus. In some embodiments, imaging apparatus 122*a* or 122*b* may be a 2-Dimensional (2D) imaging apparatus such as a digital camera. In some embodiments, imaging apparatus 122*a* or 122*b* may be more advanced, such as incorporating Optical Coherence Tomography (OCT) and/or Fluorescence Lifetime Imaging Microscopy (FLIM). For example, in some embodiments, imaging apparatus 122*a* or 122*b* may be a retinal sensing device may be configured for widefield or scanning retina fundus imaging such as using white light or infrared (IR) light, fluorescence intensity, OCT, or fluorescence lifetime data. Alternatively or additionally, imaging apparatus 122*a* or 122*b* may be configured for one-dimensional (1D), 2-dimensional (2D), 3-dimensional (3D) or other dimensional contrast imaging. Herein, fluorescence and lifetime are considered different dimensions of contrast. Images described herein may be captured using any or each of a red information channel (e.g., having a wavelength between 633-635 nm), a green information channel (e.g., having a wavelength of approximately 532 nm), or any other suitable light imaging channel(s). As a non-limiting example, a fluorescence excitation wavelength may be between 480-510 nm with an emission wavelength from 480-800 nm.

Imaging apparatus 122*a* or 122*b* may be packaged separately from other components of device 120*a* or 120*b*, such that it may be positioned near a person's eye(s). In some embodiments, device 120*a* or device 120*b* may be configured to accommodate (e.g., conform to, etc.) a person's face, such as specifically around the person's eye(s). Alternatively, device 120*a* or 120*b* may be configured to be held in front of the person's eye(s). In some embodiments, a lens of imaging apparatus 122*a* or 122*b* may be placed in front of the user's eye during imaging of the person's retina fundus. In some embodiments, imaging apparatus 122*a* or 122*b* may be configured to capture one or more images in response to a user pressing a button on device 120*a* or 120*b*. In some embodiments, imaging apparatus 122*a* or 122*b* may be configured to capture the image(s) responsive to a voice command from the user. In some embodiments, imaging apparatus 122*a* may be configured to capture the image(s) responsive to a command from computer 140. In some embodiments, imaging apparatus 122*a* or 122*b* may be configured to capture the image(s) automatically upon device 120*a* or 120*b* sensing the presence of the person, such as by detecting the person's retina fundus in view of imaging apparatus 122*a* or 122*b*.

The inventors have also developed novel and improved imaging apparatus having enhanced imaging functionality and a versatile form factor. In some embodiments, imaging apparatus described herein may include two or more imaging devices, such as OCT and/or FLIM devices within a common housing. For example, a single imaging apparatus may include a housing shaped to support OCT and FLIM devices within the housing along with associated electronics for performing imaging and/or accessing the cloud for image storage and/or transmission. In some embodiments, electronics onboard the imaging apparatus may be configured to perform various processing tasks described herein, such as identifying a user of the imaging apparatus (e.g., by imaging the person's retina fundus), accessing a user's electronic health records, and/or determine a health status or medical condition of the user.

In some embodiments, imaging apparatus described herein may have a form factor that is conducive to imaging both of a person's eyes (e.g., simultaneously). In some embodiments, imaging apparatus described herein may be configured for imaging each eye with a different imaging device of the imaging apparatus. For example, as described further below, the imaging apparatus may include a pair of lenses held in a housing of the imaging apparatus for aligning with a person's eyes, and the pair of lenses may also be aligned with respective imaging devices of the imaging apparatus. In some embodiments, the imaging apparatus may include a substantially binocular shaped form factor with an imaging device positioned on each side of the imaging apparatus. During operation of the imaging apparatus, a person may simply flip the vertical orientation of the imaging apparatus (e.g., by rotating the device about an axis parallel to the direction in which imaging is performed). Accordingly, the imaging apparatus may transition from imaging the person's right eye with a first imaging device to imaging the right eye with a second imaging device, and likewise, transition from imaging the person's left eye with the second imaging device to imaging the left eye with the first imaging device. In some embodiments, imaging apparatus described herein may be configured for mounting on a table or desk, such as on a stand. For example, the stand may permit rotation of the imaging apparatus about one or more axes to facilitate rotation by a user during operation.

It should be appreciated that aspects of the imaging apparatus described herein may be implemented using a different form factor than substantially binocular shaped. For instance, embodiments having a form factor different than substantially binocular shaped may be otherwise configured in the manner described herein in connection with the exemplary imaging apparatus described below. For example, such imaging apparatus may be configured to image one or both of a person's eyes simultaneously using one or more imaging devices of the imaging apparatus.

Figure 14A:
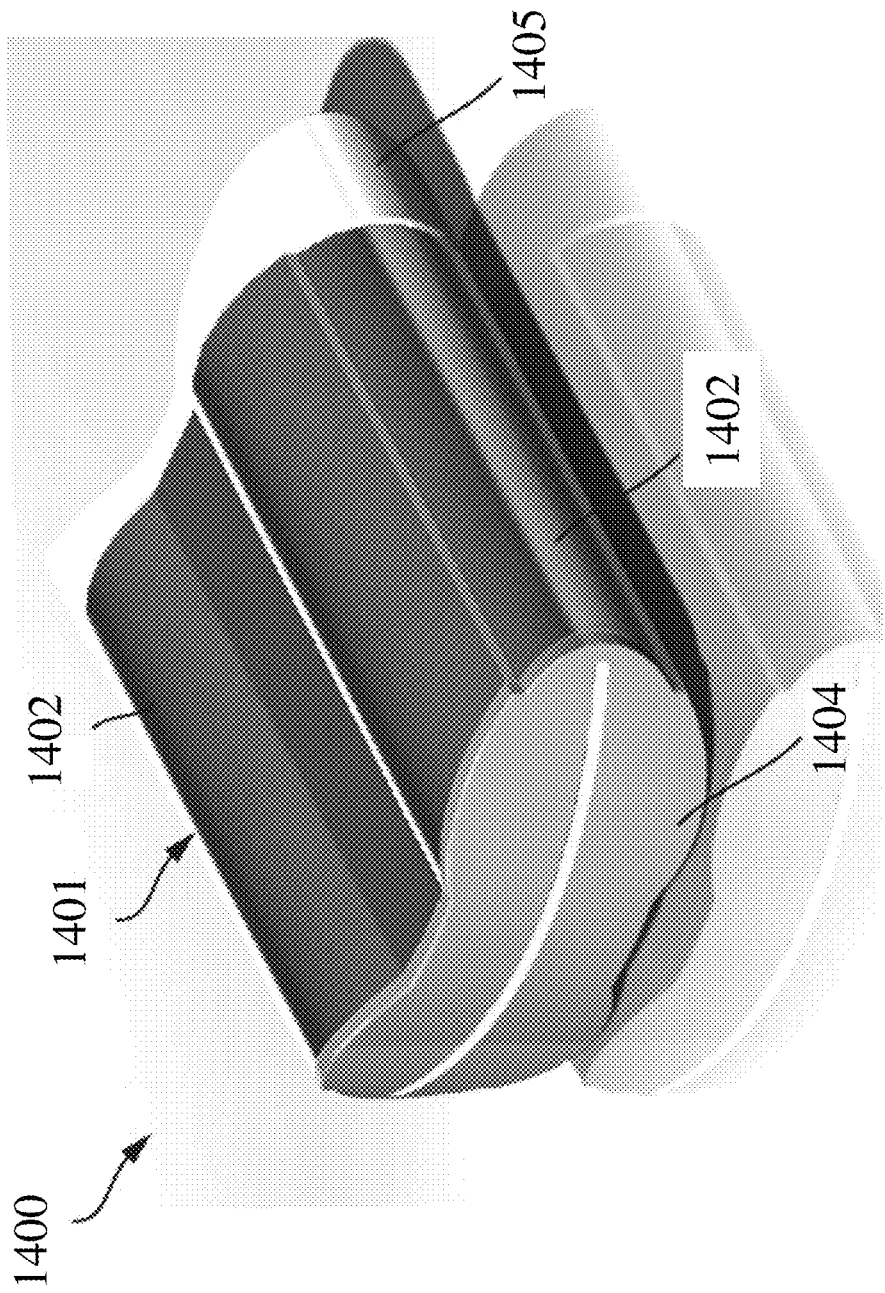
FIG. 14A is a front perspective view of an exemplary imaging apparatus, in accordance with some embodiments of the technology described herein.
Figure 14B:
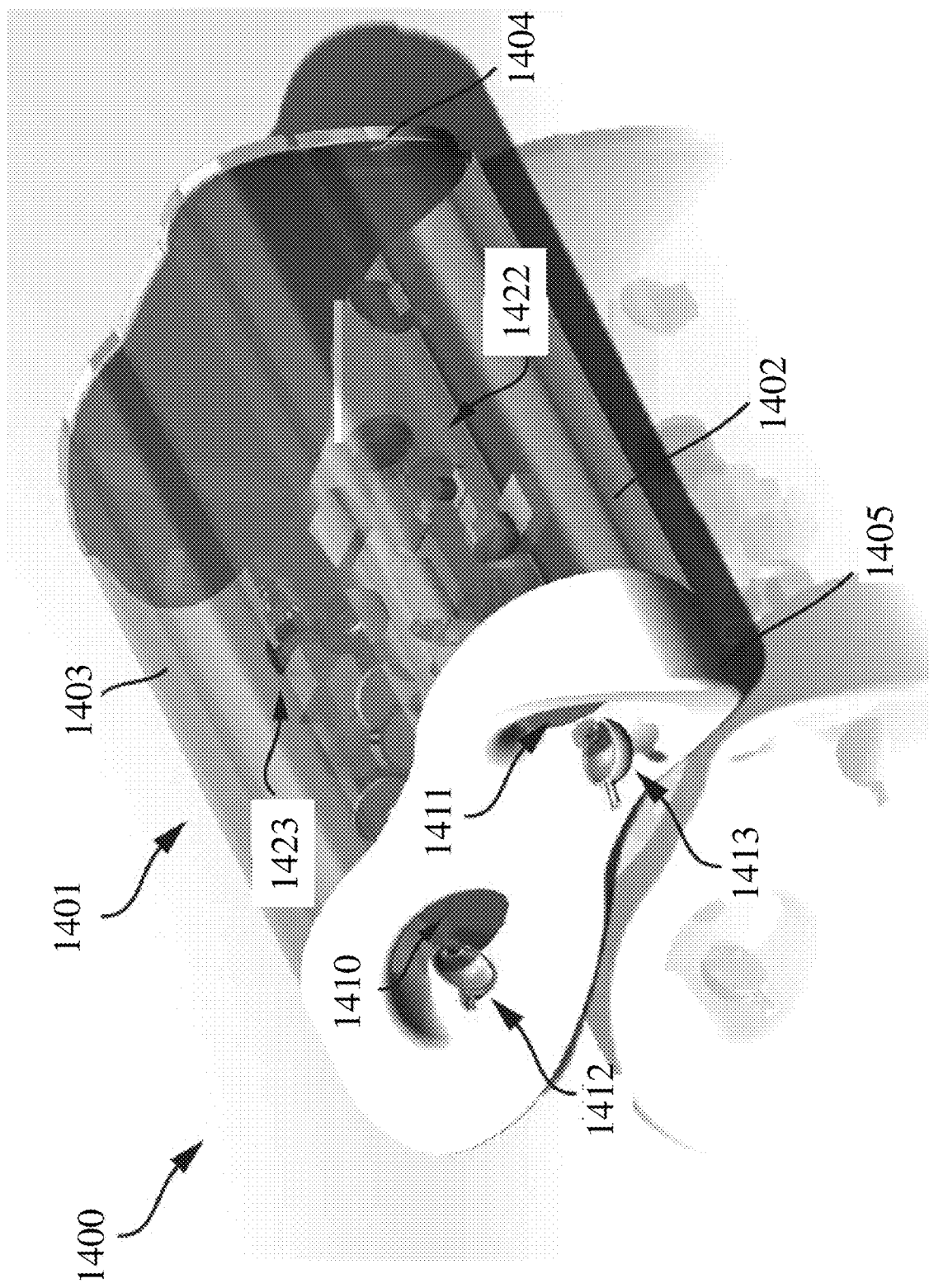
FIG. 14B is a rear perspective, and partly transparent view of the imaging apparatus of FIG. 14A, in accordance with some embodiments of the technology described herein.

One example of an imaging apparatus according to the technology described herein is illustrated in FIGS. 14A-14B. As shown in FIG. 14A, imaging apparatus 1400 includes a housing 1401 with a first housing section 1402 and a second housing section 1403. In some embodiments, the first housing section 1402 may accommodate a first imaging device 1422 of the imaging apparatus 1400, and the second housing section 1403 may accommodate a second imaging device 1423 of the imaging apparatus. As illustrated in FIGS. 14A-14B, housing 1401 is substantially binocular shaped.

In some embodiments, the first and second imaging devices 1422 may include an optical imaging device, a fluorescent imaging device, and/or an OCT imaging device. For example, in one embodiment, the first imaging device 1422 may be an OCT imaging device, and the second imaging device 1423 may be an optical and fluorescent imaging device. In some embodiments, the imaging apparatus 1400 may include only a single imaging device 1422 or 1423, such as only an optical imaging device or only a fluorescent imaging device. In some embodiments, first and second imaging devices 1422 and 1423 may share one or more optical components such as lenses (e.g., convergent, divergent, etc.), mirrors, and/or other imaging components. For instance, in some embodiments, first and second imaging devices 1422 and 1423 may share a common optical path. It is envisioned that the devices may operate independently or in common. Each may be an OCT imaging device, each may be a fluorescent imaging device, or both may be one or the other. Both eyes may be imaged and/or measured simultaneously, or each eye may be imaged and/or measured separately.

Housing sections 1402 and 1403 may be connected to a front end of the housing 1401 by a front housing section 1405. In the illustrative embodiment, the front housing section 1405 is shaped to accommodate the facial profile of a person, such as having a shape that conforms to a human face. When accommodating a person's face, the front housing section 1405 may further provide sight-lines from the person's eyes to the imaging devices 1422 and/or 1423 of the imaging apparatus 1400. For example, the front housing section 1405 may include a first opening 1410 and a second opening 1411 that correspond with respective openings in the first housing section 1402 and the second housing section 1403 to provide minimally obstructed optical paths between the first and second optical devices 1422 and 1423 and the person's eyes. In some embodiments, the openings 1410 and 1410 may be covered with one or more transparent windows (e.g., each having its own window, having a shared window, etc.), which may include glass or plastic.

First and second housing sections 1402 and 1403 may be connected at a rear end of the housing 1401 by a rear housing section 1404. The rear housing section 1404 may be shaped to cover the end of the first and second housing sections 1402 and 1403 such that light in an environment of the imaging apparatus 1400 does not enter the housing 1401 and interfere with the imaging devices 1422 or 1423.

In some embodiments, imaging apparatus 1400 may be configured for communicatively coupling to another device, such as a mobile phone, desktop, laptop, or tablet computer, and/or smart watch. For example, imaging apparatus 1400 may be configured for establishing a wired and/or wireless connection to such devices, such as by USB and/or a suitable wireless network. In some embodiments, housing 1401 may include one or more openings to accommodate one or more electrical (e.g., USB) cables. In some embodiments, housing 1401 may have one or more antennas disposed thereon for transmitting and/or receiving wireless signals to or from such devices. In some embodiments, imaging devices 1422 and/or 1423 may be configured for interfacing with the electrical cables and/or antennas. In some embodiments, imaging devices 1422 and/or 1423 may receive power from the cables and/or antennas, such as for charging a rechargeable battery disposed within the housing 1401.

During operation of the imaging apparatus 1400, a person using the imaging apparatus 1400 may place the front housing section 1405 against the person's face such that the person's eyes are aligned with openings 1410 and 1411. In some embodiments, the imaging apparatus 1400 may include a gripping member (not shown) coupled to the housing 1401 and configured for gripping by a person's hand. In some embodiments, the gripping member may be formed using a soft plastic material, and may be ergonomically shaped to accommodate the person's fingers. For instance, the person may grasp the gripping member with both hands and place the front housing section 1405 against the person's face such that the person's eyes are in alignment with openings 1410 and 1411. Alternatively or additionally, the imaging apparatus 1400 may include a mounting member (not shown) coupled to the housing 1401 and configured for mounting the imaging apparatus 1400 to a mounting arm, such as for mounting the imaging apparatus 1400 to a table or other equipment. For instance, when mounted using the mounting member, the imaging apparatus 1400 may be stabilized in one position for use by a person without the person needing to hold the imaging apparatus 1400 in place.

In some embodiments, the imaging apparatus 1400 may employ a fixator, such as a visible light projection from the imaging apparatus 1400 towards the person's eyes, such as along a direction in which the openings 1410 and 1411 are aligned with the person's eyes, for example. In accordance with various embodiments, the fixator may be a bright spot, such as a circular or elliptical spot, or an image, such as an image or a house or some other object. The inventors recognized that a person will typically move both eyes in a same direction to focus on an object even when only one eye perceives the object. Accordingly, in some embodiments, the image apparatus 1400 may be configured to provide the fixator to only one eye, such as using only one opening 1410 or 1411. In other embodiments, fixators may be provided to both eyes, such as using both openings 1410 and 1411.

Figure 15:
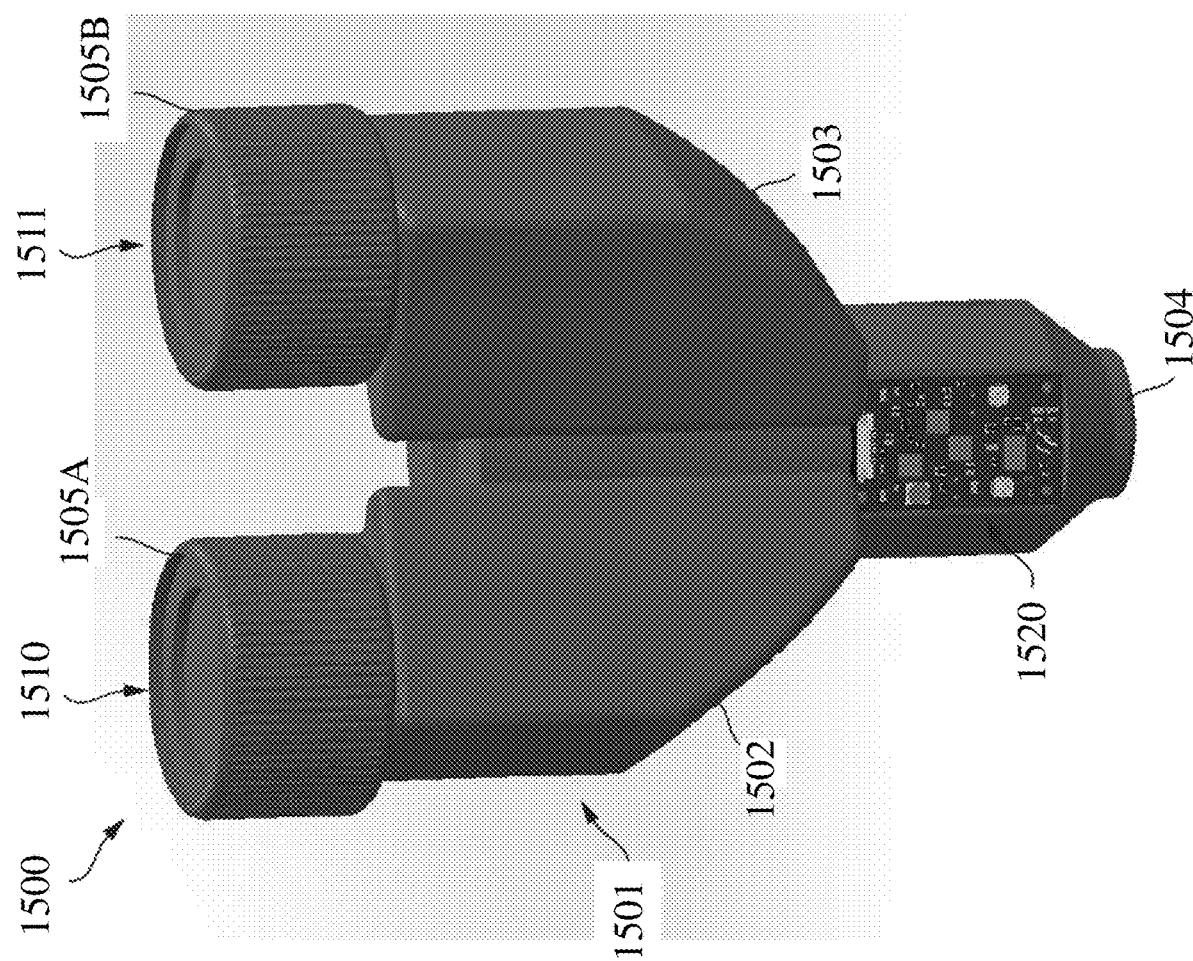
FIG. 15 is a bottom view of an alternative exemplary imaging apparatus, in accordance with some embodiments of the technology described herein.

FIG. 15 illustrates a further embodiment of an imaging apparatus 1500, in accordance with some embodiments. As shown, imaging apparatus 1500 includes housing 1501, within which one or more imaging devices (not shown) may be disposed. Housing 1501 includes first housing section 1502 and second housing section 1503 connected to a central housing portion 1504. The central housing portion 1504 may include and/or operate as a hinge connecting the first and second housing sections 1502 and 1503, and about which the first and second housing portions 1502 and 1503 may rotate. By rotating the first and/or second housing sections 1502 and/or 1503 about the central housing portion 1504, a distance separating the first and second housing sections 1502 and 1503 may be increased or decreased accordingly. Before and/or during operation of the imaging apparatus 1500, a person may rotate the first and second housing sections 1502 and 1503 to accommodate a distance separating the person's eyes, such as to facilitate alignment of the person's eyes with openings of the first and second housing sections 1502 and 1503.

The first and second housing sections 1502 and 1503 may be configured in the manner described for first and second housing sections 1402 and 1403 in connection with FIGS. 14A-14B. For instance, each housing section may accommodate one or more imaging devices therein, such as an optical imaging device, a fluorescent imaging device, and/or an OCT imaging device. In FIG. 15, each housing section 1502 and 1503 is coupled to a separate one of front housing sections 1505A and 1505B. Front housing sections 1505A and 1505B may be shaped to conform to the facial profile of a person using the imaging apparatus 1500, such as conforming to portions of the person's face proximate the person's eyes. In one example, the front housing sections 1505A and 1505B may be formed using a pliable plastic that may conform to the person's facial profile when placed against the person's face. Front housing sections 1505A and 1505B may have respective openings 1511 and 1510 that correspond with openings of first and second housing sections 1502 and 1503, such as in alignment with the openings of the first and second housing sections 1502 and 1503 to provide minimally obstructed optical paths from the person's eyes to the imaging devices of the imaging apparatus 1500. In some embodiments, the openings 1510 and 1511 may be covered with a transparent window made using glass or plastic.

In some embodiments, the central housing section 1504 may include one or more electronic circuits (e.g., integrated circuits, printed circuit boards, etc.) for operating the imaging apparatus 1500. In some embodiments, one or more processors of device 120a and/or 120b may be disposed in central housing section 1504, such as for analyzing data captured using the imaging devices. The central housing section 1504 may include wired and/or wireless means of electrically communicating to other devices and/or computers, such as described for imaging apparatus 1400. For instance, further processing (e.g., as described herein) may be performed by the devices and/or computers communicatively coupled to imaging apparatus 1500. In some embodiments, the electronic circuits onboard the imaging apparatus 1500 may process captured image data based on instructions received from such communicatively coupled devices or computers. In some embodiments, the imaging apparatus 1500 may initiate an image capture sequence based on instructions received from a devices and/or computers communicatively coupled to the imaging apparatus 1500. In some embodiments, processing functionality described herein for device 120a and/or 120b may be performed using one or more processors onboard the imaging apparatus.

As described herein including in connection with imaging apparatus 1400, imaging apparatus 1500 may include a gripping member and/or a mounting member, and/or a fixator.

Figure 16A:
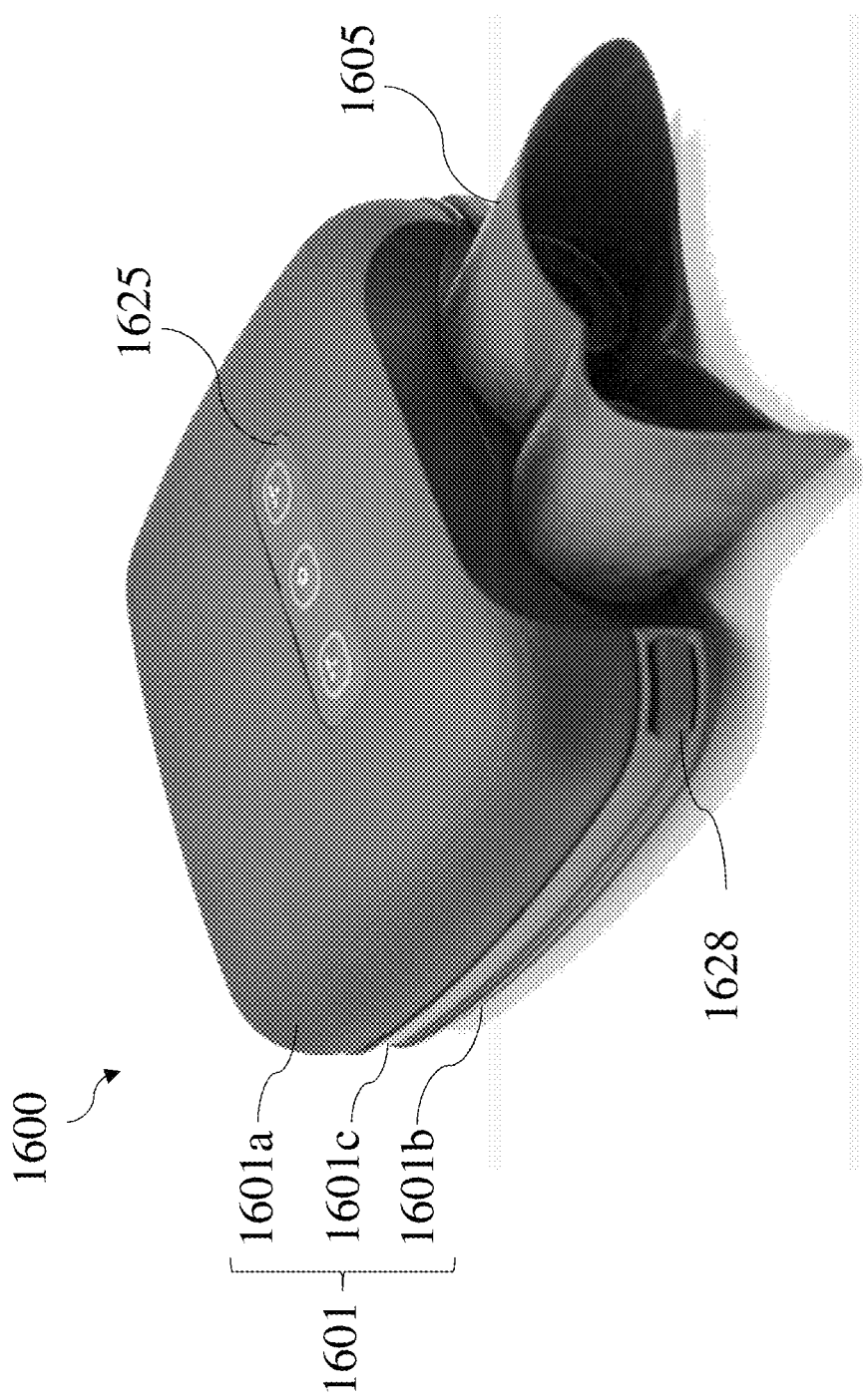
FIG. 16A is a rear perspective view of a further exemplary imaging apparatus, in accordance with some embodiments of the technology described herein.
Figure 16B:
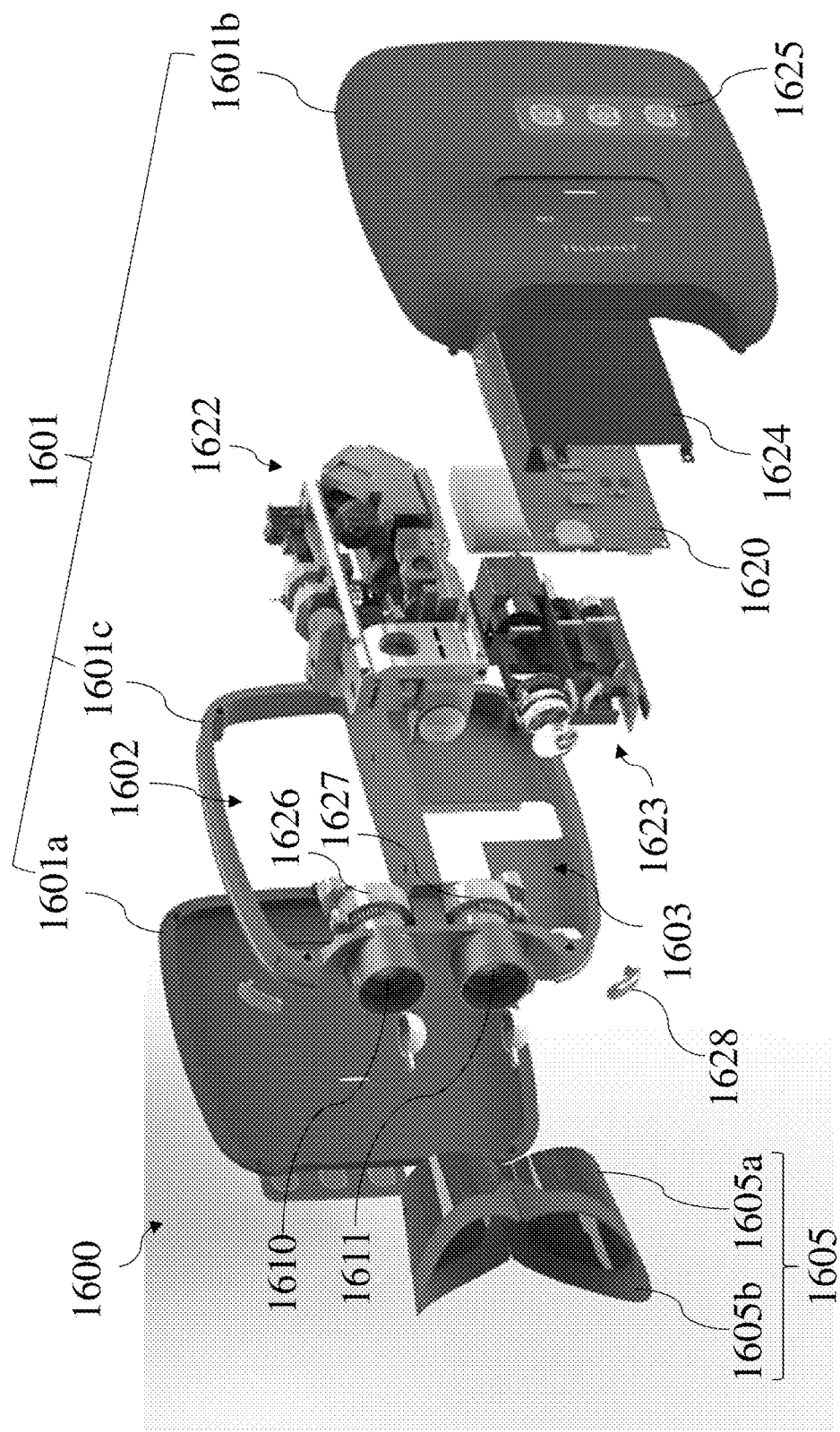
FIG. 16B is an exploded view of the imaging apparatus of FIG. 16A, in accordance with some embodiments of the technology described herein.
Figure 16D:
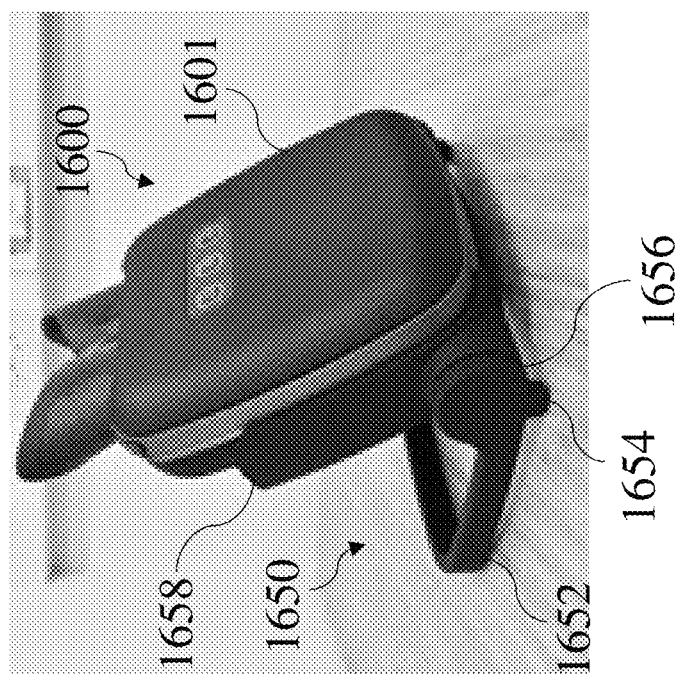
FIG. 16D is a perspective view of the imaging apparatus of FIG. 16A supported by a stand, in accordance with some embodiments of the technology described herein.
Figure 16C:
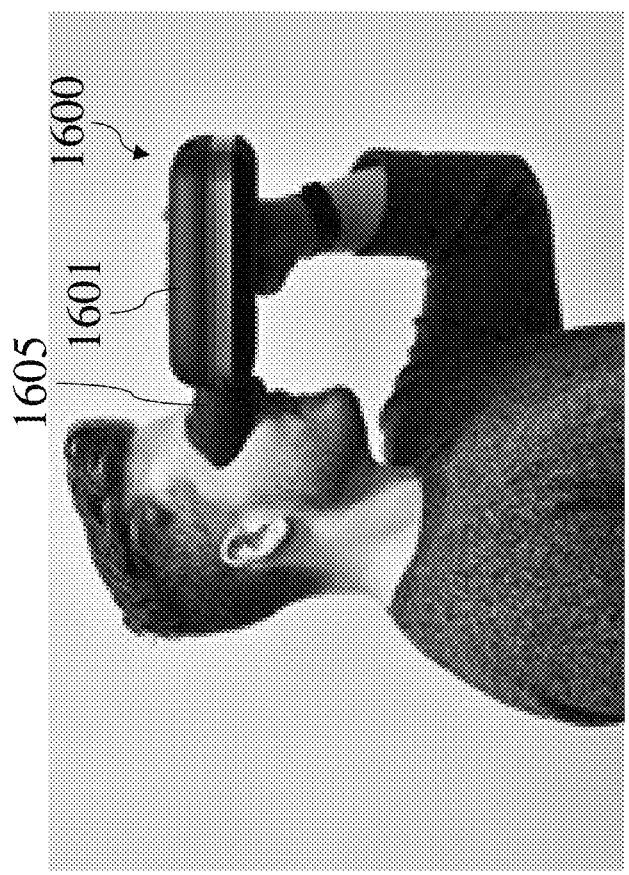
FIG. 16C is a side view of a person using the imaging apparatus of FIG. 16A to image one or each of the person's eyes, in accordance with some embodiments of the technology described herein.

FIGS. 16A-16D illustrate a further embodiment of an imaging apparatus 1600, according to some embodiments. As shown in FIG. 16A, imaging apparatus 1600 has a housing 1601, including multiple housing portions 1601a, 1601b, and 1601c. Housing portion 1601a has a control panel 1625 including multiple buttons for turning imaging apparatus 1600 on or off, and for initiating scan sequences. FIG. 16B is an exploded view of imaging apparatus 1600 illustrating components disposed within housing 1601, such as imaging devices 1622 and 1623 and electronics 1620. Imaging devices 1622 and 1623 may include an optical imaging device, a fluorescent imaging device, and/or an OCT imaging device, in accordance with various embodiments, as described herein in connection with FIGS. 14A-14B and 15. Imaging apparatus further includes front housing portion 1605 configured to receive a person's eyes for imaging, as illustrated, for example, in FIG. 16C. FIG. 16D illustrates imaging apparatus 1600 seated in stand 1650, as described further herein.

As shown in FIGS. 16A-16D, housing portions 1601a and 1601b may substantially enclose imaging apparatus 1600, such as by having all or most of the components of imaging apparatus 1600 disposed between housing portions 1601a and 1601b. Housing portion 1601c may be mechanically coupled to housing portions 1601a and 1601b, such as using one or more screws fastening the housing 1601 together. As illustrated in FIG. 16B, housing portion 1601c may have multiple housing portions therein, such as housing portions 1602 and 1603 for accommodating imaging devices 1622 and 1623. For example, in some embodiments, the housing portions 1602 and 1603 may be configured to hold imaging devices 1622 and 1623 in place. Housing portion 1601c is further includes a pair of lens portions in which lenses 1610 and 1611 are disposed. Housing portions 1602 and 1603 and the lens portions may be configured to hold imaging devices 1622 and 1623 in alignment with lenses 1610 and 1611. Housing portions 1602 and 1603 may accommodate focusing parts 1626 and 1627 for adjusting the foci of lenses 1610 and 1611. Some embodiments may further include securing tabs 1628. By adjusting (e.g., pressing, pulling, pushing, etc.) securing tabs 1628, housing portions 1601a, 1601b, and/or 1601c may be decoupled from one another, such as for access to components of imaging apparatus 1600 for maintenance and/or repair purposes.

Electronics 1620 may be configured in the manner described for electronics 1620 in connection with FIG. 15. Control panel 1625 may be electrically coupled to electronics 1520. For example, the scan buttons of control panel 1625 may be configured to communicate a scan command to electronics 1620 to initiate a scan using imaging device 1622 and/or 1623. As another example, the power button of control panel 1625 may be configured to communicate a power on or power off command to electronics 1620. As illustrated in FIG. 16B, imaging apparatus 1600 may further include electromagnetic shielding 1624 configured to isolate electronics 1620 from sources of electromagnetic interference (EMI) in the surrounding environment of imaging apparatus 1600. Including electromagnetic shielding 1624 may improve operation (e.g., noise performance) of electronics 1620. In some embodiments, electromagnetic shielding 1624 may be coupled to one or more processors of electronics 1620 to dissipate heat generated in the one or more processors.

In some embodiments, imaging apparatus described herein may be configured for mounting to a stand, as illustrated in the example of FIG. 16D. In FIG. 16D, imaging apparatus 1600 is supported by stand 1650, which includes base 1652 and holding portion 1658. Base 1652 is illustrated including a substantially U-shaped support portion and has multiple feet 1654 attached to an underside of the support portion. Base 1652 may be configured to support imaging apparatus 1600 above a table or desk, such as illustrated in the figure. Holding portion 1658 may be shaped to accommodate housing 1601 of imaging apparatus 1600. For example, an exterior facing side of holding portion 1658 may be shaped to conform to housing 1601.

As illustrated in FIG. 16D, base 1652 may be coupled to holding portion 1658 by a hinge 1656. Hinge 1656 may permit rotation about an axis parallel to a surface supporting base 1652. For instance, during operation of imaging apparatus 1600 and stand 1650, a person may rotate holding portion 1658, having imaging apparatus 1600 seated therein, to an angle comfortable for the person to image one or both eyes. For example, the person may be seated at a table or desk supporting stand 1650. In some embodiments, a person may rotate imaging apparatus 1600 about an axis parallel to an optical axis along which imaging devices within imaging apparatus image the person's eye(s). For instance, in some embodiments, stand 1650 may alternatively or additionally include a hinge parallel to the optical axis.

In some embodiments, holding portion 1658 (or some other portion of stand 1650) may include charging hardware configured to transmit power to imaging apparatus 1600 through a wired or wireless connection. In one example, the charging hardware in stand 1650 may include a power supply coupled to one or a plurality of wireless charging coils, and imaging apparatus 1600 may include wireless charging coils configured to receive power from the coils in stand 1650. In another example, charging hardware in stand 1650 may be coupled to an electrical connector on an exterior facing side of holding portion 1658 such that a complementary connector of imaging apparatus 1600 interfaces with the connector of stand 1650 when imaging apparatus 1600 is seated in holding portion 1658. In accordance with various embodiments, the wireless charging hardware may include one or more power converters (e.g., AC to DC, DC to DC, etc.) configured to provide an appropriate voltage and current to imaging apparatus 1600 for charging. In some embodiments, stand 1650 may house at least one rechargeable battery configured to provide the wired or wireless power to imaging apparatus 1600. In some embodiments. Stand 1650 may include one or more power connectors configured to receive power from a standard wall outlet, such as a single-phase wall outlet.

In some embodiments, front housing portion 1605 may include multiple portions 1605a and 1605b. Portion 1605a may be formed using a mechanically resilient material whereas front portion 1605b may be formed using a mechanically compliant material, such that front housing portion 1605 is comfortable for a user to wear. For example, in some embodiments, portion 1605a may be formed using plastic and portion 1605b may be formed using rubber or silicone. In other embodiments, front housing portion 1605 may be formed using a single mechanically resilient or mechanically compliant material. In some embodiments, portion 1605b may be disposed on an exterior side of front housing portion 1605, and portion 1605a may be disposed within portion 1605b.

The inventors have recognized several advantages which may be gained by capturing multiple images of the person's retina fundus. For instance, extracting data from multiple captured images facilitates biometric identification techniques which are less costly to implement while also being less susceptible to fraud. As described herein including with reference to section III, data extracted from captured images may be used to identify a person by comparing the captured image data against stored image data. In some embodiments, a positive identification may be indicated when the captured image data has at least a predetermined degree of similarity to some portion of the stored image data. While a high predetermined degree of similarity (e.g., close to 100%) may be desirable to prevent the system from falsely identifying a person, such a high degree of required similarity conventionally results in a high false-rejection ratio (FRR), meaning that it is more difficult for the correct person to be positively identified. This may be because, when identifying a person using a single captured image of the person having a low resolution and/or a low field-of-view, the captured image may not achieve the high predetermined degree of similarity, for example due to missing or distorted features in the image. As a result, an imaging apparatus capable of capturing images with a high resolution and a high field-of-view may be desirable to allow use of a high predetermined degree of similarity without compromising FRR. However, a high quality imaging apparatus capable of supporting a high predetermined degree of similarity is typically more expensive than a simple digital camera. The conventional alternative to using a more expensive imaging apparatus is to use a lower predetermined degree of similarity. However, such a system may be more susceptible to fraud.

To solve this problem, the inventors have developed techniques for biometric identification which may be performed using an ordinary digital camera for enhanced flexibility. In contrast to single-image comparison systems, the inventors have developed systems which may capture multiple images for comparison, which facilitates use of a higher degree of similarity without requiring a higher resolution or field-of-view imaging apparatus. In some embodiments, data may be extracted from multiple images of the person's retina fundus and combined into a single set for comparison. For example, multiple images may be captured by imaging apparatus 122a or 122b, each of which may be slightly rotated from one another so as to capture different portions of the person's retina fundus. In some embodiments, the person's eye(s) may rotate and/or may track imaging apparatus 122a or 122b. Accordingly, data indicative of features of the person's retina fundus may be extracted from the images and combined into a dataset indicative of locations of the various features. Because multiple images are combined for use, no single captured image needs to be high resolution or have a high field of view. Rather, a simple digital camera, such as a digital camera integrated with a mobile phone, may be used for imaging as described herein.

In some embodiments, system 100 or 120b may be configured to verify retina fundus identification using recorded biometric characteristics (e.g., multi-factor identification). For example, device 120a or 120b may also include one or more biometric sensors such as a fingerprint reader and/or a microphone. Thus, device 120a or 120b may record one or more biometric characteristics of a person, such as a fingerprint and/or a voiceprint of the person. Data indicative of features of the biometric characteristic(s) may be extracted in the manner described for retina fundus images, and in the case of device 120a, the data may be transmitted to computer 140 for verification. Accordingly, once an identification is made based on the retina fundus image(s), the biometric characteristic data may be compared against stored characteristic data associated with the person to verify the retina fundus identification for added security.

II. Techniques for Identifying a Person Based on a Retinal Image

Figure 3:
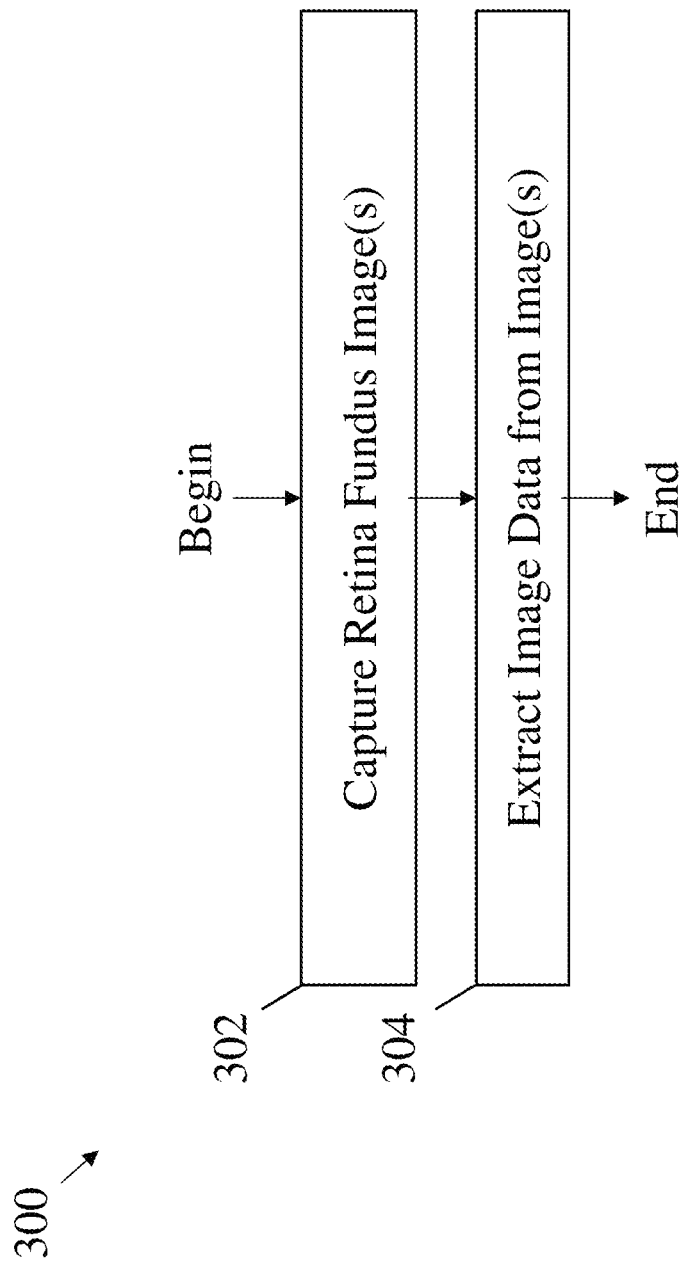
FIG. 3 is a flow diagram illustrating an exemplary method for capturing one or more retina fundus images and extracting image data from the captured image(s), in accordance with the embodiments of FIGS. 1-2.
Figure 4:
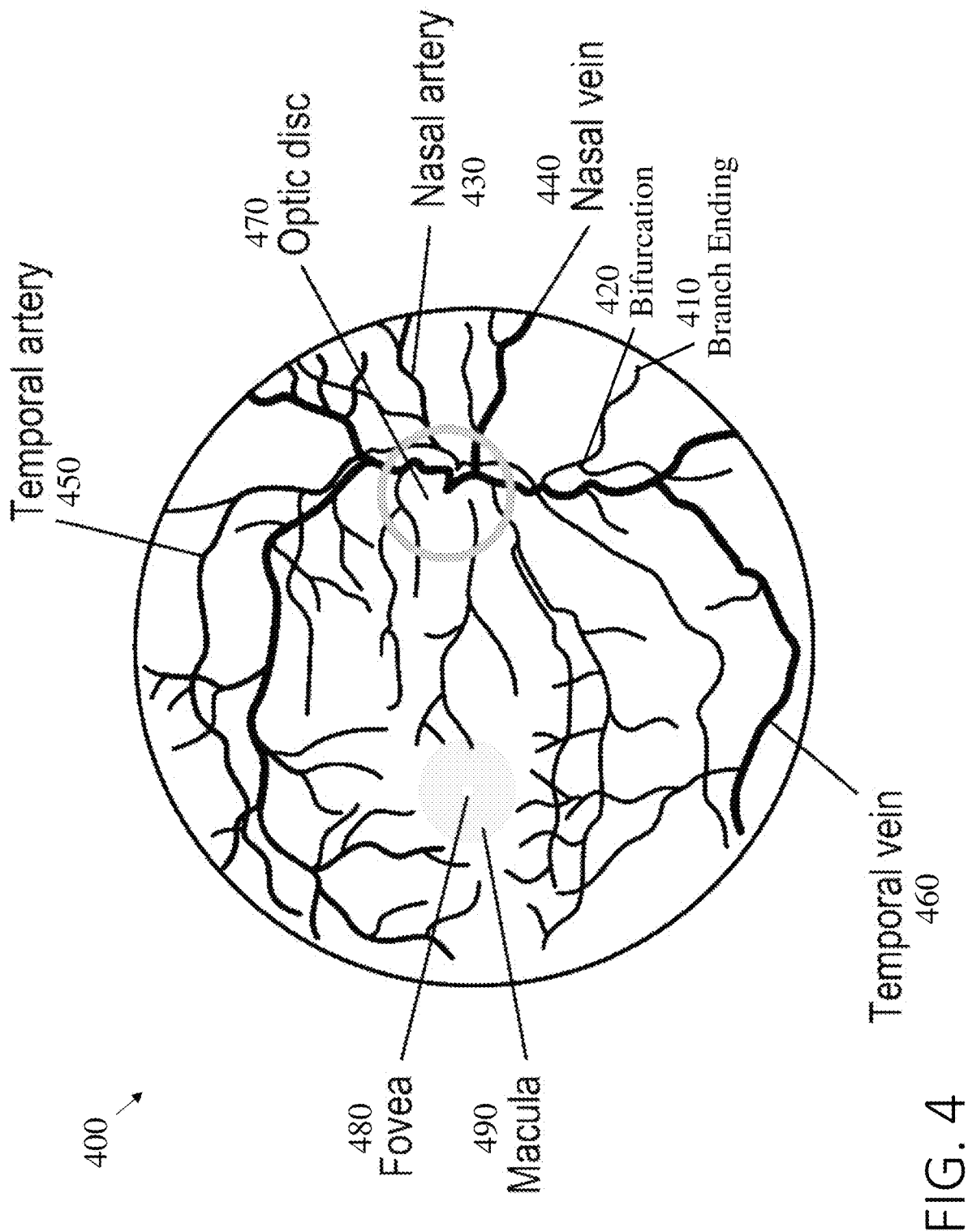
FIG. 4 is a side view of a person's retina fundus including various features which may be captured in one or more image(s) and/or indicated in data extracted from the image(s), in accordance with the method of FIG. 3.
Figure 5:
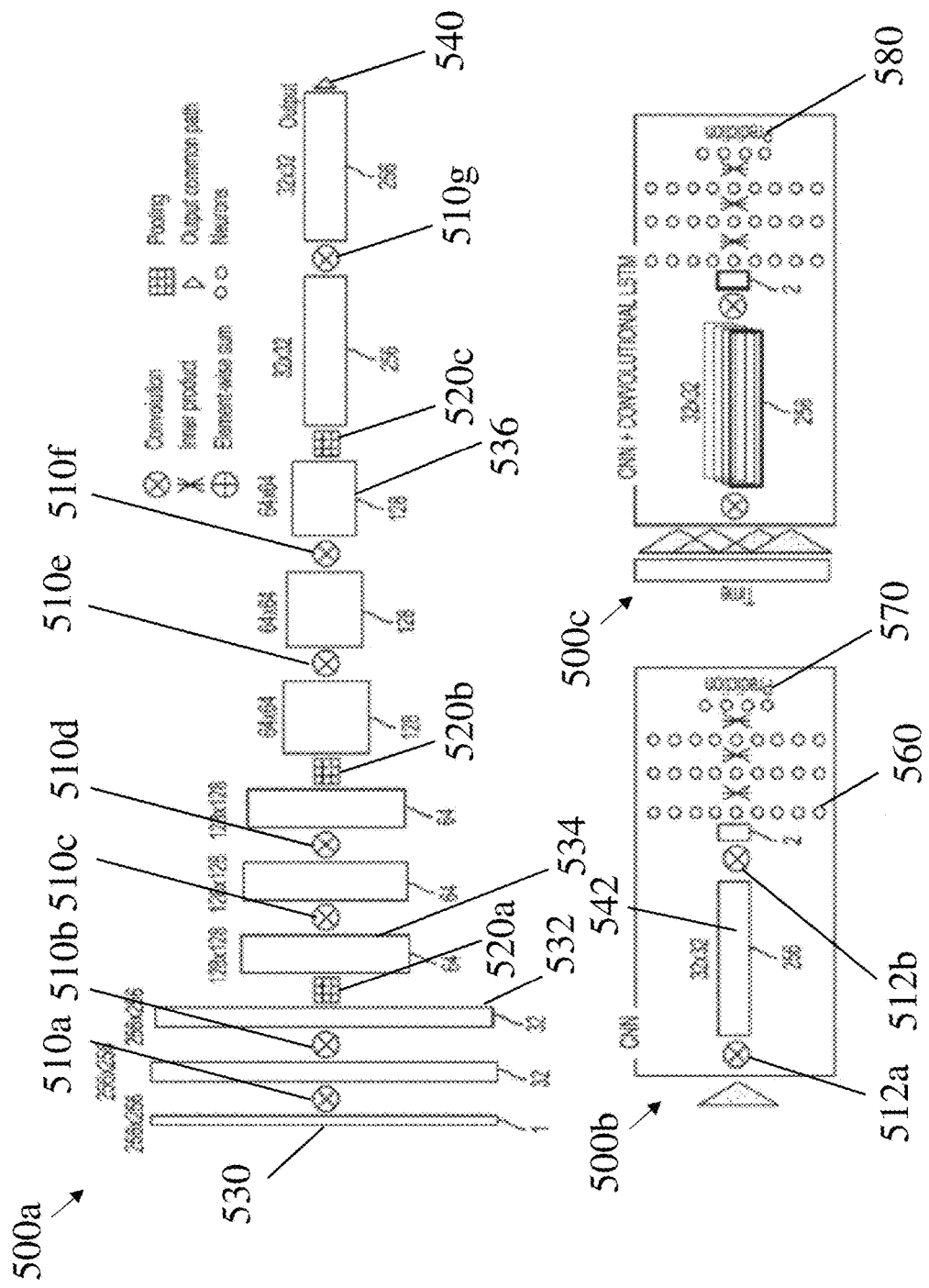
FIG. 5A is a block diagram of an exemplary convolutional neural network (CNN), in accordance with some embodiments of the method of FIG. 3.
FIG. 5B is a block diagram of an exemplary convolutional neural network (CNN), in accordance with some embodiments of the CNN of FIG. 5A.
FIG. 5C is a block diagram of an exemplary recurrent neural network (RNN) including a long short-term memory (LSTM) network, in accordance with alternative embodiments of the CNN of FIG. 5A.

The inventors have developed techniques for identifying a person based on a retinal image of the person. The technique may include comparing data extracted from one or more captured images of the person's retina fundus to stored data extracted from other retina fundus images. Techniques for extracting data from one or more captured images is described herein including with reference to FIGS. 3-4. FIG. 3 provides an illustrative method for capturing one or more images of a person's retina fundus and extracting data from the captured image(s), and FIG. 4 illustrates some features of a person's retina fundus which may be indicated in data extracted from the image(s).

FIG. 3 is a flow diagram illustrating exemplary method 300 including capturing one or more retina fundus images at step 302 and extracting image data from the image(s) at step 304. In accordance with the embodiment of FIG. 1, method 300 may be performed by device 120a, or alternatively may be performed in part by device 120a and in part by computer 140. In accordance with the embodiment of FIG. 2, method 300 may be performed entirely by device 120b.

Capturing the image(s) at step 302 may be performed in accordance with any or all embodiments of the technology described in section I. Extracting image data from the image(s) at step 304 may include processor 124a or 124b obtaining the captured image(s) from imaging apparatus 122a or 122b and extracting data indicative of features of the person's retina fundus from the image(s). For example, the data may include relative positions and orientations of the features. In some embodiments, feature data may be extracted from multiple captured images and combined into a single feature dataset. It should be appreciated that feature extraction at step 304 may be performed by computer 140. For example, in some embodiments of system 100, device 120a may be configured to capture the image(s) and to transmit the image(s) to computer 140 for data extraction.

Also during step 304, the extracted data may be recorded on a storage medium, such as storage medium 124 of device 120b. In some embodiments of cloud-based system 100, imaging apparatus 122a may capture the image(s) and/or extract data from the image(s) when device 120a does not have access to communication network 160, and so processor 124a may store the image(s) and/or data on the storage medium at least until a time when it may be transmitted over communication network 160. In such cases, processor 124a may obtain the image(s) and/or data from the storage medium shortly before transmitting the image(s) and/or data to computer 140. In some embodiments, the retina fundus image(s) may not be captured by device 120a or 120b, but by a separate device. The image(s) may be transferred to device 120a or 120b, from which data may be extracted and stored on the storage medium. Alternatively, the data may also be extracted by the separate device and transferred to device 120a or to device 120b. For example, device 120a may be tasked with passing the data to computer 140, or device 120b may identify a person or perform some other task based on the data.

FIG. 4 is a side view of retina fundus 400 including various features which may be captured in one or more images at step 302 during method 300 of FIG. 3, and/or may be indicated in data extracted from the image(s) at step 304. For example, features of veins and arteries of retina fundus 400 may be used to identify a person. Such features may include branch endings 410 and bifurcations 420 of the veins and arteries. The inventors have recognized that, similar to in fingerprinting, locations of branch endings 410 and bifurcations 420 (sometimes referred to as "minutiae") may be used as unique identifiers. Accordingly, in some embodiments, relative locations of branch endings 410 and/or bifurcations 420 may be extracted from a single captured image and recorded in one or more datasets. In some instances, relative locations of branch endings 410 and/or bifurcations 420 may be extracted from multiple captured images and combined into a single dataset. For example, an average relative location of each branch ending 410 and/or bifurcation 420 may be recorded in the dataset. In some embodiments, relative locations of specific veins or arteries such as nasal artery 430, nasal vein 440, temporal artery 450, and/or temporal vein 460 may be recorded in one or more datasets.

In some embodiments, data indicative of other features may be extracted instead of or in addition to data for branch endings 410 and/or bifurcations 420 at step 304. For example, aspects of optic disc 470 or optic disc edges such as a relative position within retina fundus 400 may be recorded in a dataset. In some embodiments, data associated with optic disc 470 may be recorded in a separate dataset from data associated with veins or arteries. Alternatively or additionally, data indicative of a relative position of fovea 480 and/or macula 490 may be recorded in a dataset. Further features which may be indicated in data extracted from the captured image(s) include the optic nerve, blood vessel surroundings, AV nicks, drusen, retinal pigmentations, and others.

In some embodiments, extracting any or all of the features described above may include solving segmentation of the image(s) into a full spatial map including relative positions and orientations of the individual features. For example, the spatial map may include a binary mask indicative of whether features such as branch endings 410 or bifurcations 420 are present at any particular location in the map. In some embodiments, a relative angle indicating locations of the features may be calculated based on the spatial map. To conserve storage space and/or simplify computing of the spatial map, thickness of some features such as veins may be reduced to a single pixel width. Alternatively or additionally, redundant data may be removed from the spatial map, such as data resulting from a combination of multiple images.

In some embodiments, the feature data may include relative positions and orientations of translationally and rotationally invariant features to facilitate a Scale Invariant Feature Transform (SIFT) and/or Speeded Up Robust Feature (SURF) comparison, as described herein including with reference to section III. For example, the extracted features described above may be Scale Invariant Feature Transform (SIFT) features and/or Speeded Up Robust Features (SURF).

The inventors have also developed techniques for extracting data from one or more captured images using a trained statistical classifier (TSC), in accordance with the embodiments illustrated in FIGS. 5A-5C, 6, and 7A-7B. For example, in some embodiments, step 304 of method 300 may be performed by a TSC such as illustrated in the embodiments of FIGS. 5A-5C, 6, and 7A-7B. One or more images(s) captured by imaging apparatus 122a or 122b may be input to the TSC. The captured image(s) may include data from one or more widefield or scanned retinal images collected from imaging apparatus 122a or 122b such as by white light, IR, fluorescence intensity, OCT, or 1D, 2D or 3D fluorescence lifetime data. The TSC may be configured to identify and output aspects of various retina fundus features in the image(s). The inventors have recognized that implementing TSCs for extracting feature data from captured images facilitates identification using multiple captured images. For example, TSCs described herein may be configured to form predictions based on individual images or groups of images. The predictions may be in the form of one or more outputs from the TSC. Each output may correspond to a single image or to multiple images. For example, one output may indicate the likelihood of a particular retina fundus feature appearing in one or more locations in a given image. Alternatively, the output may indicate the likelihood of multiple features appearing in one or more locations of the image. Further, the output may indicate the likelihood of a single feature or of multiple features appearing in one or more locations in multiple images.

TSCs described herein may be implemented in software, in hardware, or using any suitable combination of software and hardware. For example, a TSC may be executed on processor 124a of device 120a, processor 144 of computer 140, and/or processor 124b of device 120b. In some embodiments, one or more machine learning software libraries may be used to implement TSCs as described herein such as Theano, Torch, Caffe, Keras, and TensorFlow. These libraries may be used for training a statistical classifier such as a neural network, and/or for implementing a trained statistical classifier.

In some embodiments, data extraction using a TSC may take place on device 120a, which may transmit the output of the TSC to computer 140 over communication network 160. Alternatively, computer 140 may obtain the captured image(s) from device 120a and extract the captured image data from the captured image(s), for example using a TSC executed on computer 140. In accordance with the latter embodiment, device 120a may be configured to transmit the captured image(s) to computer 140 in the form of one or more compressed versions of the image(s), such as standardized by the Joint Photographic Experts Group (JPEG), or alternatively as one or more uncompressed versions such as by Portable Network Graphic (PNG). In the embodiment of FIG. 2, device 120b may obtain the captured image data from the captured image by extraction, such as using a TSC executed on processor 124b.

Figure 6:
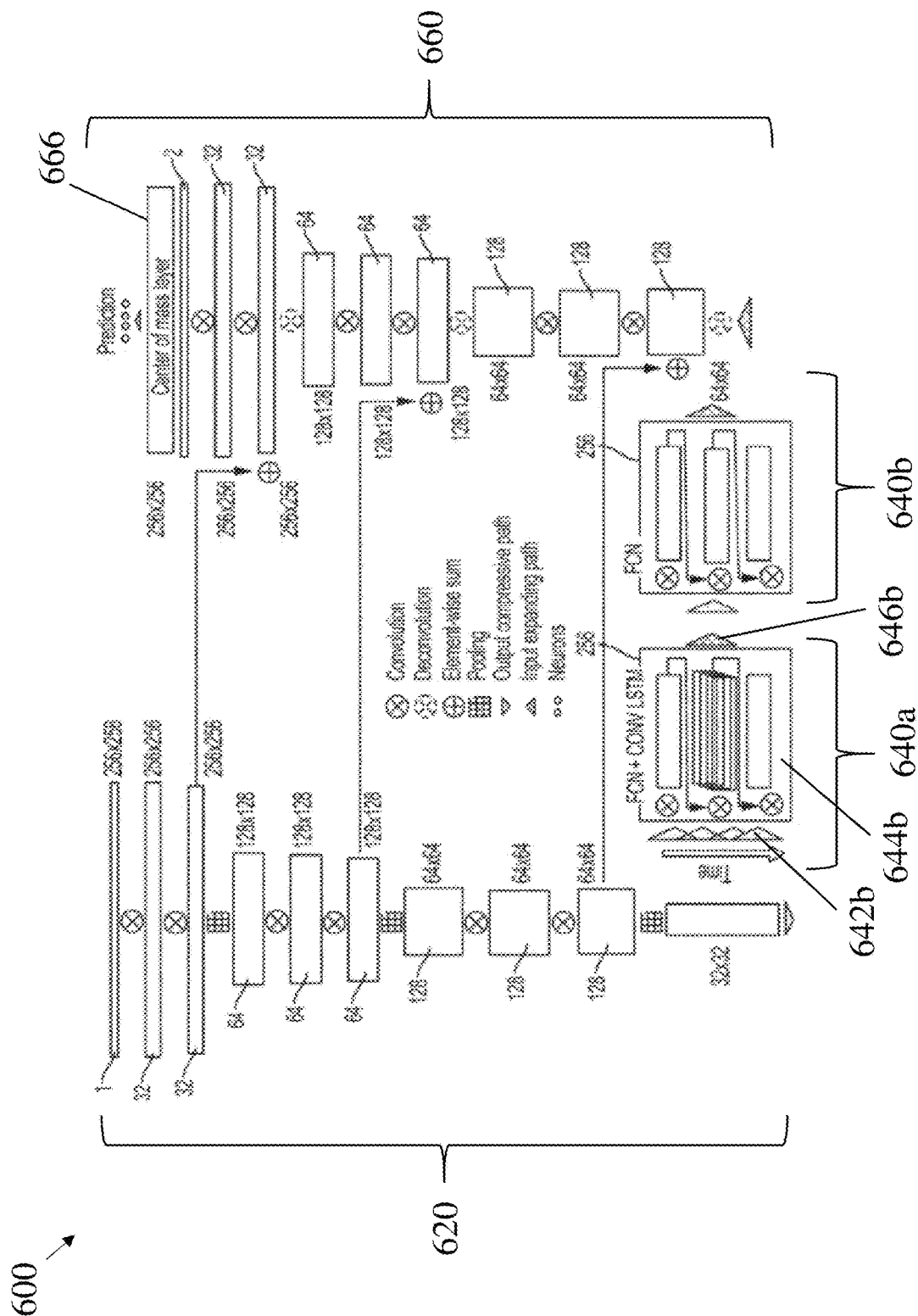
FIG. 6 is a block diagram of an exemplary fully convolutional neural network (FCNN), in accordance with some embodiments of the method of FIG. 3.
Figure 7:
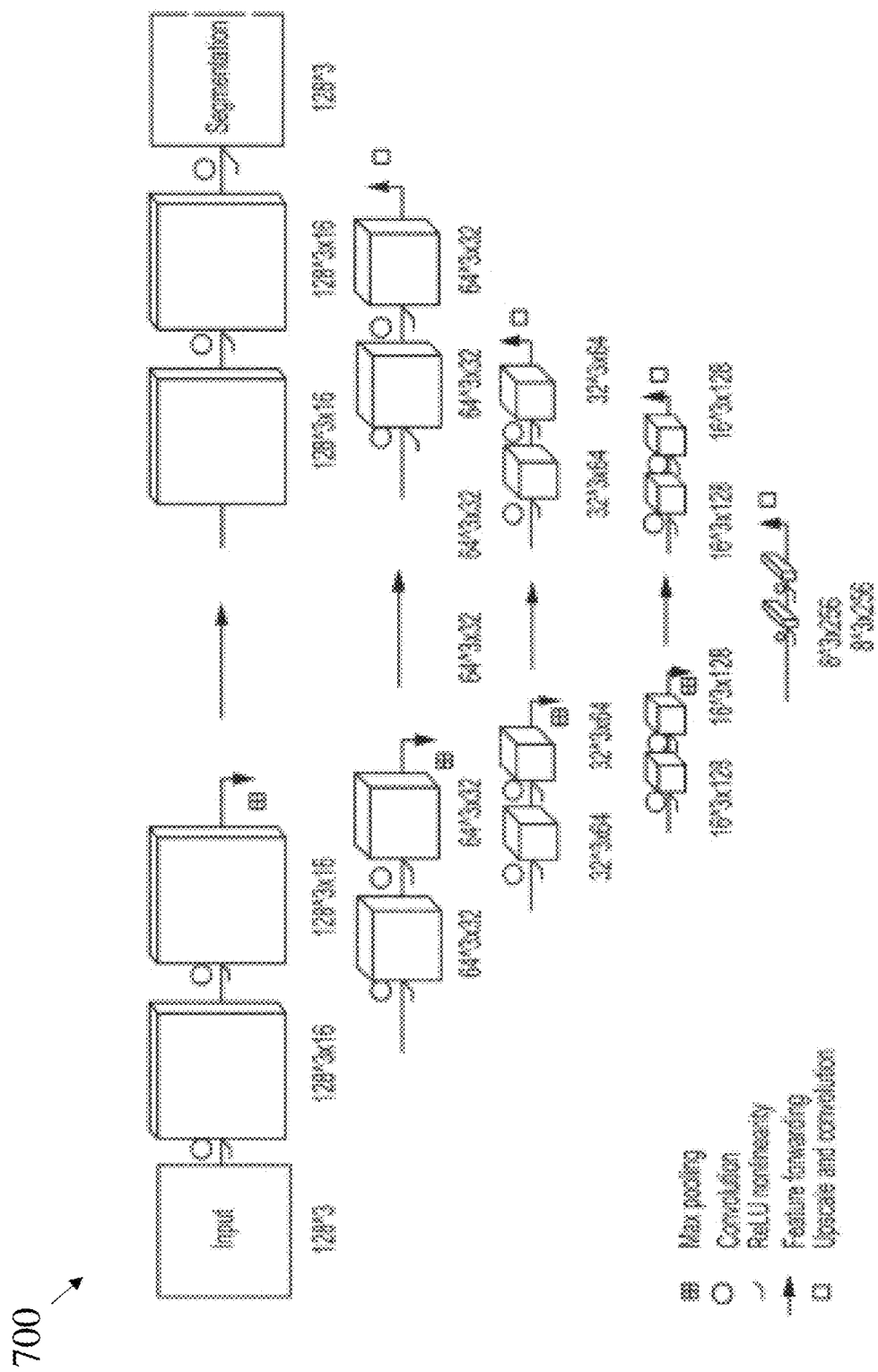
FIG. 7 is a block diagram of an exemplary convolutional neural network (CNN), in accordance with alternative embodiments of the method of FIG. 3.
Figure 8:
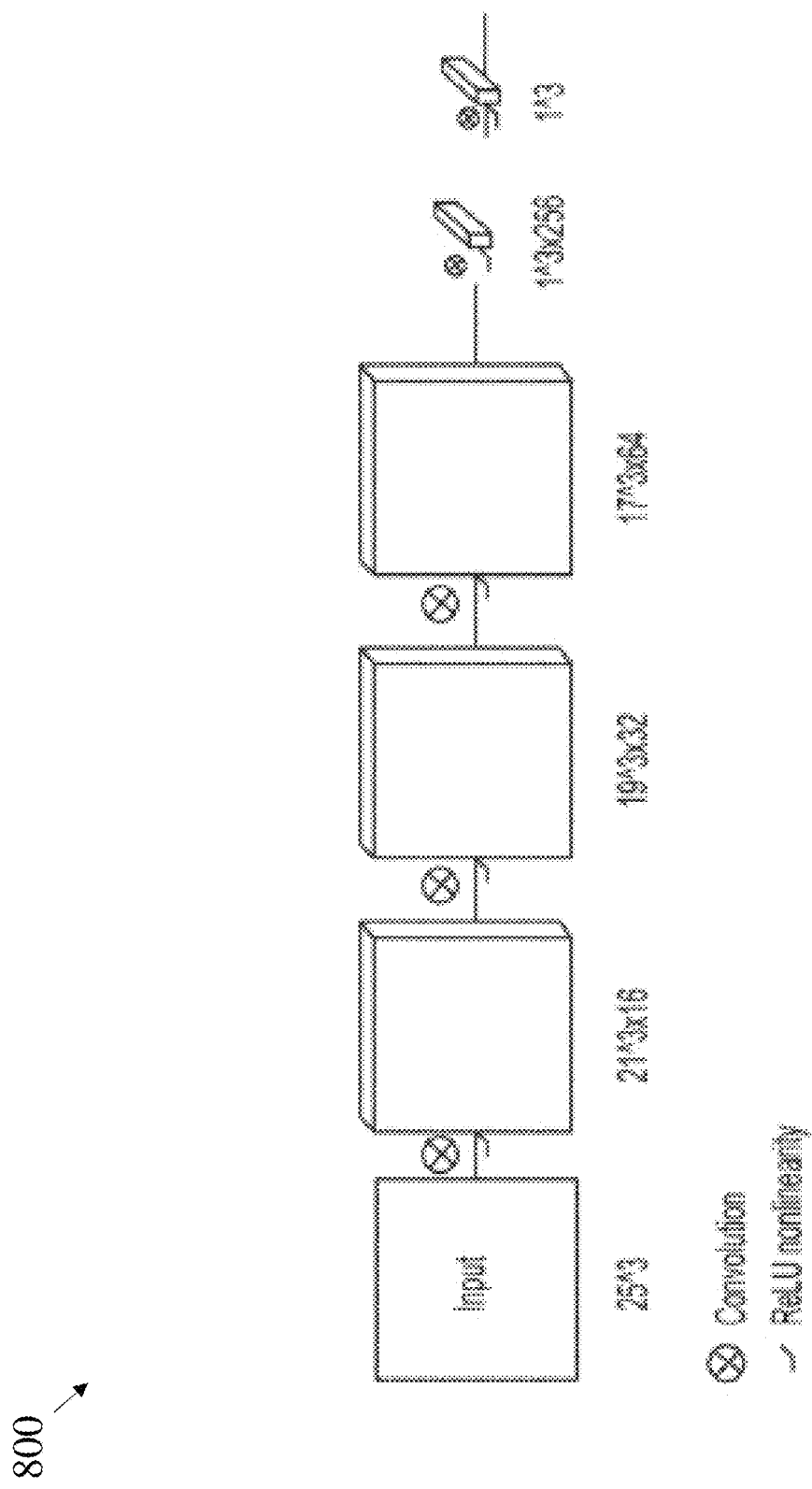
FIG. 8 is a block diagram of an exemplary convolutional neural network (CNN), in accordance with further alternative embodiments of the method of FIG. 3.

FIGS. 5A-5C, 6, and 7-8 illustrate aspects of neural network statistical classifiers for use in biometric security systems described herein. In accordance with the illustrative embodiments of FIGS. 5A-5B, a neural network statistical classifier may include a convolutional neural network (CNN). In accordance with the illustrative embodiments of FIGS. 5A and 5C, the neural network statistical classifier may further include a recurrent neural network (RNN), such as a long short-term memory (LSTM) network. Alternatively, in accordance with the illustrative embodiment of FIG. 6, the neural network statistical classifier may include a fully convolutional neural network (FCNN). FIG. 7 illustrates an FCNN configured to identify boundaries of features in an image of a person's retina fundus. FIG. 8 illustrates a CNN configured to identify individual voxels which has the advantage of higher invariance to locations of various retina fundus features such as blood vessels.

FIGS. 5A and 5B are block diagrams of portions 500a and 500b forming an exemplary convolutional neural network (CNN) configured to extract data from a captured image of a person's retina fundus. In the illustrative embodiment of FIGS. 5A and 5B, portion 500a may be operatively coupled to portion 500b, such as with an output of portion 500a coupled to an input of portion 500b.

As shown in FIG. 5A, portion 500a of the CNN includes an alternating series of convolutional layers 510a-510g and pooling layers 520a-520c. Image 530, which may be a 256 pixel by 256 pixel (256×256) image of a person's retina fundus, is provided as an input to portion 500a. Portion 500a may be configured to obtain feature map 540 from image 530, and to output feature map 540 to portion 500b. Portion 500b may be configured to generate predictions 570 to indicate aspects of image 530, such as locations of retina fundus features.

Prior to being input to portion 500a, image 530 may be pre-processed, such as by resampling, filtering, interpolation, affine transformation, segmentation, erosion, dilation, metric calculations (i.e. minutia), histogram equalization, scaling, binning, cropping, color normalization, resizing, reshaping, background subtraction, edge enhancement, corner detection, and/or using any other suitable pre-processing techniques. Examples of pre-processing techniques include:
1. Rescale the images to have the same radius (e.g., 300 pixels),
2. Subtract the local average color,
    e.g., with the local average mapped to 50% gray
3. Clip the images to a portion (e.g., 90%) of their size to remove boundary effects.
  This may include cropping the images to contain only retina pixels and testing the effect of histogram equalization on the performance of the algorithm.
4. Crop the images to contain mostly retina pixels
    (note; if using this, there may not be a need to rescale the image based on radius.)

In some embodiments, image 530 may be a compressed or uncompressed version of an image captured by imaging apparatus 122a or 122b. Alternatively, image 530 may be processed from one or more images captured by imaging apparatus 122a or 122b. In some embodiments, image 530 may include post-image reconstruction retina data such as one or more 3D volumetric OCT images. Alternatively or additionally, image 530 may include unprocessed portions of the captured image(s). For example, image 530 may include spectra from one or more spectral-domain OCT images, fluorescence lifetime statistics, pre-filtered images, or pre-arranged scans. In some embodiments, image 530 may be associated with multiple 2D images corresponding to slices of the person's retina fundus. In some embodiments, the slices may be neighboring. For example, in accordance with various embodiments, image 530 may be associated with images corresponding to two, three, four, or five respective neighboring slices. In some embodiments, image 530 may include one or more 2D images of one or more respective slices in which the blood vessels are prominent.

CNN 500a is configured to process image 530 through convolutional layers 510a-510g and pooling layers 520a-520c. In some embodiments, convolutional layers 510a-510g and pooling layers 520a-520c may be trained to detect aspects of retina fundus features in a captured image. First, CNN 500a processes image 530 using convolutional layers 510a and 510b to obtain 32 256×256 feature maps 532. Next, after an application of pooling layer 520a, which may be a max pooling layer, convolutional layers 510c and 510d are applied to obtain 64 128×128 feature maps 534. Next, after an application of pooling layer 520b, which may also be a max pooling layer, convolutional layers 510e and 510f are applied to obtain 128 64×64 feature maps 536. Next, after application of pooling layer 520c and convolutional layer 510g, resulting 256 32×32 feature maps 538 may be provided at output 540 as an input for portion 500b of the CNN illustrated in FIG. 5B. CNN portion 500a may be trained using gradient descent, stochastic gradient descent, backpropagation, and/or other iterative optimization techniques.

In some embodiments, CNN 500a may be configured to process a single image, such as a single slice of a person's retina fundus, at a time. Alternatively, in some embodiments, CNN 500a may be configured to process multiple images, such as multiple neighboring slices from a 3D volumetric image, at the same time. The inventors have recognized that aspects such as branch endings, bifurcations, overlaps, sizings, or other such features may be computed using information from a single slice or from multiple neighboring slices. In some embodiments, convolutions performed by convolutional layers 510a-510g on multiple slices of a person's retina fundus may be two-dimensional (2D) or three-dimensional (3D). In some embodiments, CNN 500a may be configured to predict features for each slice only using information from that particular slice. Alternatively, in some embodiments, CNN 500a may be configured to use information from that slice and also from one or more neighboring slices. In some embodiments, CNN 500a may include a fully-3D processing pipeline such that features for multiple slices are computed concurrently using data present in all of the slices.

In FIG. 5B, portion 500b includes convolutional layers 512a-512b and fully connected layers 560. Portion 500b may be configured to receive feature maps 538 from output 540 of portion 500a. For example, portion 500b may be configured to process feature maps 538 through convolutional layers 512a and 512b to obtain 256 32×32 feature maps 542. Then, feature maps 542 may be processed through fully connected layers 560 to generate predictions 570. For example, fully connected layers 560 may be configured to determine which retina fundus features are most likely to have been identified by convolutional layers 510a-510g and 512a-512b and pooling layers 520a-520c using probability distributions in feature maps 542. Accordingly, predictions 570 may indicate aspects of retina fundus features within image 530. In some embodiments, predictions 570 may include probability values such as a probabilistic heat-map corresponding to a calculated likelihood that certain features are located in certain areas of image 530. In some embodiments, predictions 570 may indicate relative locations and/or sizes of branch endings or bifurcations, or other such characteristics.

In accordance with the embodiment of FIGS. 5A-5C, portion 500c may be operatively coupled to portion 500a illustrated in FIG. 5A. For example, portion 500c may be coupled to output 540 in place of portion 500b. Portion 500a illustrated in FIG. 5A is a CNN portion, and portion 500c is a recurrent neural network (RNN) portion. Portion 500c may be used to model temporal constraints among input images provided as inputs over time. RNN portion 500c may be implemented as a long short-term memory (LSTM) neural network. Such a neural network architecture may be used to process a series of images obtained by imaging apparatus 122a or 122b during performance of a monitoring task (a longitudinal series of images over time). For example, in accordance with the embodiment of FIG. 1, device 120a may transmit the series of images to computer 140. In some embodiments, device 120a may transmit timing information of the series of images such as the time elapsed between each image in the series. The CNN-LSTM neural network of FIGS. 5A and 5C may receive the series of images as inputs and combine retina fundus features derived from at least one earlier-obtained image with features obtained from a later-obtained image to generate predictions 580.

In some embodiments, the CNN and the CNN-LSTM illustrated in FIGS. 5A-5C may use a kernel size of 3 with a stride of 1 for convolutional layers, a kernel size of "2" for pooling layers, and a variance scaling initializer. RNN portion 500c may be trained using stochastic gradient descent and/or backpropagation through time.

FIG. 6 is a block diagram of illustrative fully convolutional neural network (FCNN) 600. FCNN 600 includes output compressing portion 620 and input expanding portion 660. Output compressive portion 620 includes a series of alternating convolutional and pooling layers, which may be configured in the manner described for portion 500a of FIG. 5A. Input expanding portion 660 includes a series of alternating convolutional and deconvolutional layers, and center-of-mass layer 666. Center-of-mass layer 666 computes estimates as a center-of-mass computed from the regressed location estimates at each location.

In some embodiments, output compressing portion 620 and input expanding portion 660 are connected by processing path 640a. Processing path 640a includes a long short-term memory (LSTM) portion, which may be configured in the manner described for RNN portion 500c of FIG. 5C. Embodiments which include processing path 640a may be used to model temporal constraints in the manner described for the CNN-LSTM of FIGS. 5A and 5C. Alternatively, in accordance with other embodiments, output compressing portion 620 and input expanding portion 660 are connected by processing path 640b. In contrast to processing path 640a, processing path 640b includes a convolutional network (CNN) portion which may be configured in the manner described for CNN portion 500b of FIG. 5B.

In some embodiments, FCNN 600 may use a kernel size of 3 for convolutional layers with stride of 1, a kernel size of "2" for the pooling layers, a kernel of size 6 with stride 2 for deconvolutional layers, and a variance scaling initializer.

The output of FCNN 600 may be a single-channel output having the same dimensionality as the input. Accordingly, a map of point locations such as vessel characteristic points may be generated by introducing Gaussian kernel intensity profiles at the point locations, with FCNN 600 being trained to regress these profiles using mean-squared error loss.

FCNN 600 may be trained using gradient descent, stochastic gradient descent, backpropagation, and/or other iterative optimization techniques.

In some embodiments, TSCs described herein may be trained using labeled images. For example, the TSC may be trained using images of retina fundus features such as branch endings, bifurcations, or overlaps of blood vessels, the optic disc, vessels, bifurcations, endings, overlaps, and fovea. The scans may be annotated manually by one or more clinical experts. In some embodiments, the annotations may include indications of the locations of the vessel overlap, bifurcation, and ending points. In some embodiments, the annotations may include coverage of full structures like the full blood vessels, the optic disc, or the fovea.

The inventors have recognized that by configuring a TSC as a multi-task model, the output of the TSC may be used to identify one or more locations of features of a person's retina fundus, and also to segment the blood vessels. For example, blood vessels provide several features for identifying a person, and so it is beneficial to use blood vessel labels to train a multi-task model, such that the model is configured to identify the locations of the blood vessels more accurately. Accordingly, CNN portion 500a and/or FCNN 600 may include a multi-task model.

FIG. 7 is a block diagram of fully convolutional neural network (FCNN) 700, which may be configured to indicate locations of boundaries of certain retina fundus features such as blood vessels, optic disc, or fovea, in a captured image. Training FCNN 700 may involve zero-padding training images, using convolutional kernels of size 3 and stride 1, using a max pooling kernel with of size 2, and deconvolution (upscale and convolution) kernels with size 6 and size 2. The output of the neural network may indicate locations of boundaries of certain retina fundus features.

The inventors have recognized that some TSCs may be configured to classify individual voxels, which has the advantage of higher invariance to the location of various retina fundus features such as blood vessels. FIG. 8 is a block diagram of convolutional neural network (CNN) 800, which may be configured to indicate locations of boundaries of certain retina fundus features by classifying individual voxels. In some embodiments, CNN 800 may include convolutional kernels with size 5 and stride 1 at the first layer and kernels with size 3 in the subsequent layers. In the illustrative embodiment of FIG. 8, CNN 800 is configured for an input neighborhood of 25. In other embodiments, CNN 800 may be repeated as a building block for different sizes of the input neighborhood, such as 30 or 35. In some embodiments, larger neighborhoods may use a larger initial kernel size such as 7. Feature maps of CNN 800 may be merged in the last feature layer and combined to yield a single prediction.

In an embodiment, saliency maps are created to understand which parts of the images contribute to the output by computing the gradient of an output category with respect to input image. This quantifies how the output category value changes with respect to small changes in the input image pixels. Visualizing these gradients as an intensity image provides localization of the attention.

The computation is basically the ratio of the gradient of output category with respect to input image:

$\partial output / \partial input$

These gradients are used to highlight input regions that cause the most change in the output and thus highlight salient image regions that most contribute to the output.

It should be appreciated that the neural network architectures illustrated in FIGS. 5A-5C, 6, and 7-8 are illustrative and that variations of these architectures are possible. For example, one or more other neural network layers such as convolutional layers, deconvolutional layers, rectified linear unit layers, upsampling layers, concatenate layers, or pad layers may be introduced to any of the neural network architectures of FIGS. 5A-5C, 6, and 7-8 in addition to or instead of one or more illustrated layers. As another example, the dimensionality of one or more layers may vary, and the kernel size for one or more convolutional, pooling, and/or deconvolutional layers may also vary. In addition, TSCs described herein may alternatively or additionally include a support vector machine, a graphical model, a Bayesian classifier, or a decision tree classifier.

Figure 9:
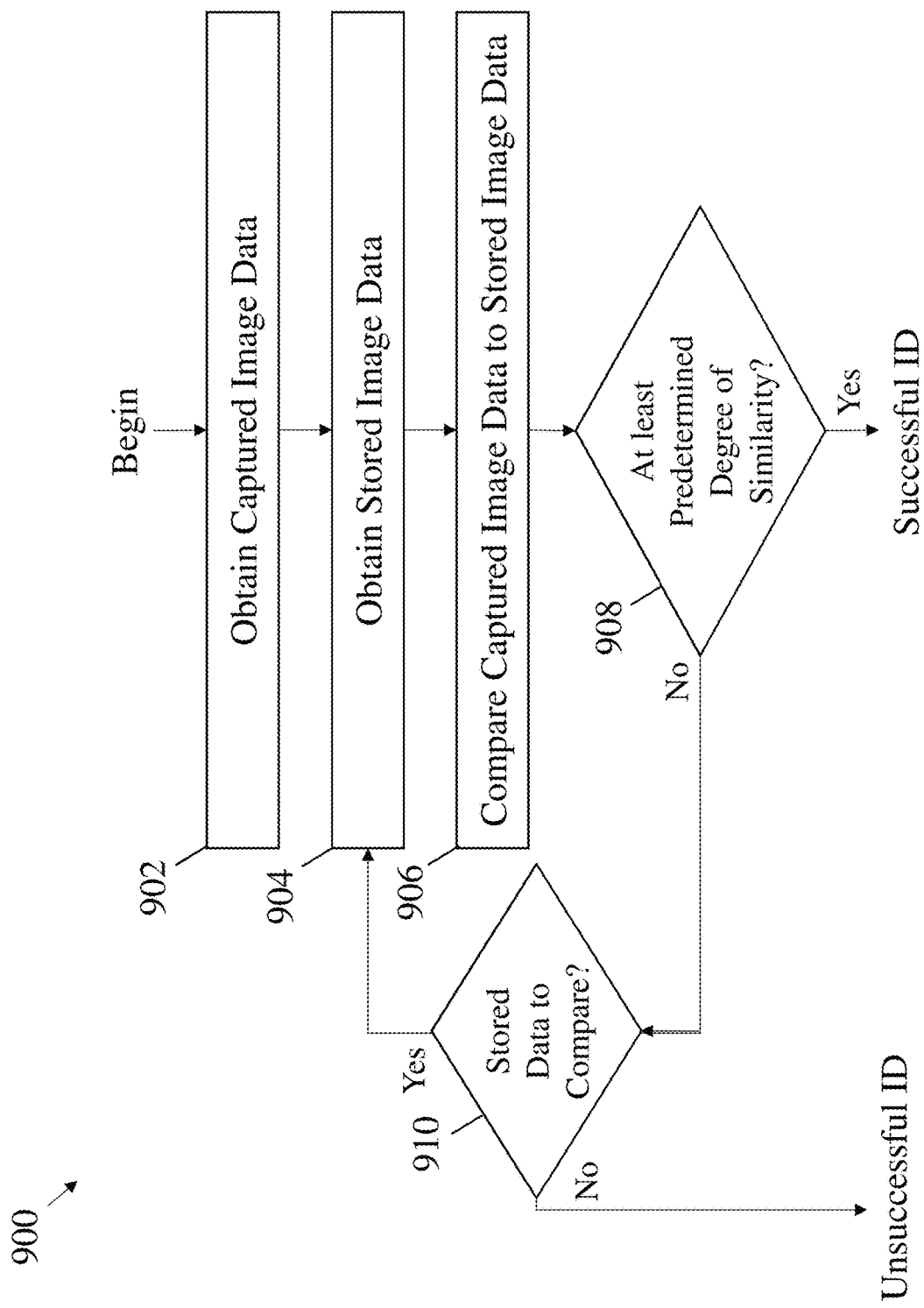
FIG. 9 is a flow diagram illustrating an exemplary method for identifying a person, in accordance with the embodiments of FIGS. 1-2.

The inventors have developed techniques for comparing data extracted from one or more captured images to stored data extracted from one or more other retina fundus images. Referring to FIG. 9, captured image data and stored image data may be obtained, and a determination may be made as to whether at least a portion of the stored image data has at least a predetermined degree of similarity to the captured image data. The captured image data and/or stored image data may be obtained by extraction using a TSC in accordance with any or all embodiments of FIGS. 5A-5C, 6, and/or 7-8. In the illustrative method of FIG. 10A, template matching is performed between the captured image data and the stored image data to generate a similarity measure. In contrast, the illustrative method of FIG. 10B includes a translationally and rotationally invariant feature comparison to generate the similarity measure.

FIG. 9 is a flow diagram of illustrative method 900 for identifying a person by comparing captured image data extracted from a captured image of the person's retina fundus to stored image data. Method 900 includes obtaining captured image data at step 902, obtaining a portion of stored image data at step 904, comparing the captured image data to the portion of stored image data at step 906, and determining whether the portion of stored image data has at least a predetermined degree of similarity to the captured image data at step 908. If the portion of stored image data is similar enough to constitute a match, method 900 concludes with a successful identification (ID). Alternatively, if the portion of stored image data is not similar enough to constitute a match, method 900 continues to step 910 to determine whether there is any stored image data which has not yet been compared to the captured image data. If so, method 900 returns to step 904 and obtains a different portion of the stored image data for comparing to the captured image data. If all stored image data has been compared to the captured image data without a successful match, method 900 concludes with an unsuccessful ID. In accordance with the embodiment of FIG. 1, method 900 may be performed by computer 140 using one or more images and/or data transmitted from device 120a. Alternatively, in accordance with the embodiment of FIG. 2, method 900 may be performed entirely by device 120b.

Obtaining captured image data at step 902 may be performed using image extraction techniques described in connection with step 304 of FIG. 3. Alternatively or additionally, the captured image data may be output from a TSC in accordance with any or all embodiments of FIG. 5A-5C, 6, or 7-8. In some embodiments, the captured image data obtained at step 902 includes all captured image data acquired for the current identification. For example, imaging apparatus 122a or 122b may capture multiple images of the person's retina fundus, and data corresponding to all retina fundus features of each of the images may be obtained at step 902. Alternatively, data corresponding to only some of the images may be obtained at step 902. As a further alternative, data corresponding to a particular retina fundus feature or set of features for each of the images may be obtained at step 902. Accordingly, in some embodiments, method 900 may return to step 902 to obtain other portions of the captured image data depending on the result of the comparison at step 906.

Obtaining stored image data at step 904 may be performed similarly to as described for captured data. The stored image data may be associated with one or more previously processed retina fundus images. For example, the stored image data may accumulate as people register with system 100 or device 120b. In some embodiments, registering a person with system 100 or device 120b may include capturing one or more image(s) of the person's retina fundus, extracting data indicative of features of the person's retina fundus from the captured image(s), and storing the extracted data on storage medium 142 or 126. In some embodiments, registering the person may include obtaining identification information such as the person's full legal name and government issued identification number (e.g., social security number). In some embodiments, the identification information is linked with contact information such as the person's telephone number and/or email address. In some embodiments, the person may also provide a username upon registering. In some embodiments, the stored image data associated with each registered person may be updated every time system 100 or device 120b successfully identifies the person. For example, when system 100 or device 120b successfully identifies a registered person, the captured image(s) used to identify the person may be added to the stored image data.

As for the captured image data, the stored image data may be processed from a 3D volumetric image, a 2D image, fluorescence lifetime data, or OCT spectral data, and may be provided to a TSC. For example, the captured image data and stored image data may be provided to a same TSC such that extracted feature data from the captured image data and the stored image data may be compared. In some embodiments, the captured image data and the stored image data are of the same type. For example, each of the captured and stored image data may include one or more 2D images of one or more retinal slices, such as neighboring slices. When the captured and stored image data are associated with a same person, the captured image data may include multiple images of neighboring slices obtained at a first time and the stored image data may include multiple images of the same neighboring slices obtained at a second time later than the first time. By way of example, the stored image data may have been processed as recently as a few minutes or as long as several years before the captured image data is acquired.

In embodiments which provide verification based on biometric characteristics in addition to retina fundus identification, one or more recorded biometric characteristics (e.g., voiceprint, fingerprint, etc.) also may be provided to the TSC in addition to or instead of the retina fundus image(s). In such circumstances, stored characteristic data associated with a plurality of biometric characteristics (e.g., for various users) may be provided to the TSC. Accordingly, the output(s) of the TSC may indicate features of the biometric characteristics to facilitate comparison of the characteristics in the manner described for retina fundus images. Thus, the TSC may also facilitate verification of the identity using biometric characteristics.

As a result of having multiple people registered with system 100 or device 120b, specific portions of the stored image data on storage medium 142 or 126 may be associated with respective people. Accordingly, obtaining the stored image data at step 904 may include obtaining a portion of the stored image data associated with a registered person. For example, all image data associated with a particular person (e.g., all data from previous successful identifications) may be obtained at step 904 for comparing to the captured image data. Alternatively, a single dataset may be obtained at step 904, for example the most recent image data acquired for that particular person, and/or data indicating aspects of a particular retina fundus feature or group of features. In some embodiments, a single dataset may be acquired at step 904 as a combination of multiple stored datasets, such as an average. In some embodiments, further portions of the stored image data may be obtained upon a return to step 902 depending on the result of the comparison at step 906.

Comparing the captured image data to the portion of stored image data at step 906 may be performed by computer 140 or device 120b. In accordance with various embodiments, the comparison may be performed using cross correlation, template matching, translationally and rotationally invariant maximized weightings, and/or distance metrics. For example, in accordance with the illustrative embodiment of FIG. 10A, computer 140 or device 120b may perform template matching between the captured image data obtained at step 902 and the stored image data at step 904 to generate a similarity measure. Alternatively, in accordance with the illustrative embodiment of FIG. 10B, computer 140 or device 120b may compare relative positions and/or orientations of translationally and rotationally invariant features of the captured image data obtained at step 902 and the stored image data obtained at step 904 to generate the similarity measure. The comparison at step 906 may compare data for all retina fundus features, or only for individual or groups of features. For example, separate comparisons may be made between aspects of an optic disc in the captured image data and in the stored image data, and aspects of blood vessels such as branch endings or bifurcations of the captured image data and the stored image data. A comparison of one aspect may be made at step 906 in one instance, and method 900 may later circle back to step 906 to perform another comparison for a different aspect.

Determining whether the portion of stored image data and the captured image data have at least a predetermined degree of similarity at step 908 may be based on the similarity measure generated at step 906. For example, the similarity measure may provide the degree of similarity between the two datasets, and step 908 may include determining whether the degree of similarity provided by the similarity measure meets the predetermined degree of similarity used as a threshold for a successful identification.

The predetermined degree of similarity may be set based on a number of factors, such as the number of captured images from which the captured image data is extracted, the resolution and field of view of the images, the number of different types of features indicated in the captured image data and the stored image data, and the comparison technique implemented at step 906. While the predetermined degree of similarity should be set relatively high to prevent fraudulent identification, such a high predetermined degree of similarity could result in a high false rejection ratio, making it more difficult to positively identify the correct person. Generally, the predetermined degree of similarity may be as high as the number of images, the resolution and field of view of the image(s), and the number of different types of features used all permit. For example, a large number of high quality captured images with many different types of features facilitate use of a higher predetermined degree of similarity without risking a high false rejection ratio. This is because there is a greater amount of information in the captured data, which may lessen the impact of imperfections in the captured image (e.g., poor lighting) or in the transmitted data (e.g., due to errors in transmission).

If the portion of stored image data has at least the predetermined degree of similarity to the stored image data, method 900 may conclude with a successful match. In some embodiments, computer 140 or device 120b may obtain identification information associated with the portion of stored image data from storage medium 142 or 126. Alternatively, computer 140 or device 120b may obtain the identification information from another location on communication network 160. For example, the identification information may be stored together with the portion of stored image data, or the stored image data may include a link to a location where the identification information is stored. In some embodiments, the identification information may include the person's full name and/or username.

In embodiments in which biometric verification is performed based on recorded biometric characteristics, comparison between captured and stored biometric characteristic data may be conducted in the manner described for retina fundus images and image data. Biometric verification is typically performed after identification information is obtained. For example, the stored biometric characteristic data may be stored with the identification information. As a result, the biometric characteristic comparison may be performed after the retina fundus identification is complete. In embodiments which use a TSC, the stored biometric characteristic data may be provided as an input to the TSC at the same time as the recorded biometric characteristic data, or alternatively afterwards. For example, the recorded biometric characteristic data may be provided to the TSC at the same time or even before the identification, with the output(s) of the TSC being saved for use after the identification is complete.

In accordance with the embodiment of FIG. 1, computer 140 may obtain and transmit the identification information to device 120a to conclude identifying the person. Device 120a or 120b may notify the person that the identification was successful, for example via a user interface generated on one or more displays. In some embodiments, device 120a or 120b may grant the person access to health information or an account associated with the person, as described herein including with reference to section III. In some embodiments, the stored image data may be updated to include some or all of the captured image data, such as data indicating retina fundus features, for future identifications.

If the portion of stored image data does not have at least the predetermined degree of similarity to the captured image data, method 900 proceeds to step 910 to determine whether there is more stored image data which has not yet been compared to the captured image data. If there is more stored image data which has not yet been compared to the captured image data, method 900 returns to step 904 and obtains a portion of the stored image data which has not yet been compared. For example, each portion of the stored image data compared to the captured image data may be associated with a registered person, and a portion of the remaining stored image data could still match the captured image data to identify the person. It should be appreciated that, in some embodiments, method 900 may return to step 902 rather than step 904. For example, the captured image data may include multiple portions corresponding to multiple captured images of the person's retina fundus, and so a different portion corresponding to one or more other captured images may be obtained at step 902 for comparing against the same stored image data previously obtained at step 904.

Alternatively, if there is no more stored image data to compare to the captured image data, method 900 may conclude with an unsuccessful identification. For example, the captured image data may correspond to a person who has not yet registered with system 100 or device 120b. In accordance with the embodiment of FIG. 1, computer 140 may notify device 120a of the unsuccessful identification, and device 120a may prompt the person to register with system 100, for example by providing identification information which may be stored with the captured image data. In accordance with the embodiment of FIG. 2, device 120b may prompt the person to register with device 120b. It should be appreciated that device 120a and 120b may not be configured to register a new user, for example in embodiments of system 100 and device 120b which may be configured to only register a new user in the presence of a healthcare professional.

Figure 10A:
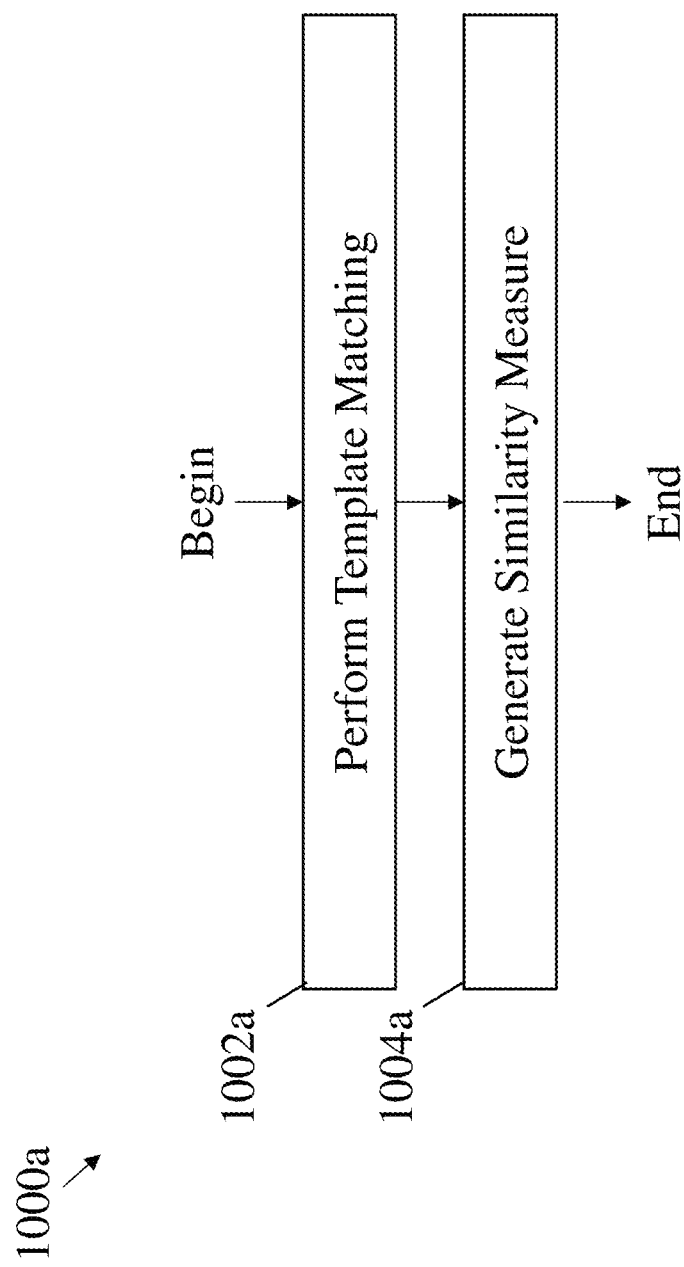
FIG. 10A is a flow diagram of a method for template-matching retina fundus features, in accordance with some embodiments of the method of FIG. 9.

FIG. 10A is a flow diagram of illustrative method 1000a for comparing captured image data to stored image data by template matching. Method 1000a includes performing template-matching at step 1002a, and generating a similarity measure at step 1004a. In some embodiments, method 1000a may be performed by device 120b or computer 140. In some embodiments, method 1000a may be performed for each subset of data stored on storage medium 142 or storage medium 126 corresponding to a single image, or to a combination of images associated with a same person.

Performing template-matching at step 1002a may include device 120b or computer 140 comparing at least a portion of the captured image data obtained at step 902 of method 900 to at least a portion of the stored image data obtained at step 904. For example, a portion of the captured image data corresponding to a region of the image(s) captured by imaging apparatus 122a or 122b may be compared against one or more portions of the stored image data corresponding to a region of one or more images from which the stored image data was extracted. During such comparison, a cross-correlation such as by convolution or other multiplication may be performed between the portion of the captured image data and the portion(s) of the stored image data. In some embodiments, the comparison includes matrix multiplication with the result being stored in a similarity matrix. The similarity matrix may be used at step 1004a for generating a similarity measure.

In some instances, the portion of the captured image(s) may be compared against the portion(s) of the stored image data, and then may be resized and/or rotated and compared against the same portion(s). The portion of the captured image data may then be compared against one or more other portions of the stored image data corresponding to other regions of the image(s) from which the stored image data was extracted. In embodiments where the stored image data is associated with multiple images, once the portion of the captured image data has been compared to all of the stored image data associated with a particular image, the portion of the captured image data may be compared to stored image data associated with a different image. Alternatively, a separate comparison may be performed for individual retina fundus features or groups of features across multiple images. Once the portion of the captured image data has been compared to all of the stored image data associated with a particular person, for example all images of the person or all data indicating various features from the images, method 1000a may proceed to generating a similarity measure at step 1004a corresponding to the particular person. For example, the similarity measure may indicate whether or not the captured image matches the particular person.

Generating a similarity measure at step 1004a may include device 120b or computer 140 calculating similarity between the captured image data obtained at step 902 of method 900 and the stored image data obtained at step 904. In some embodiments, a separate similarity measure may be calculated between the captured image data and each portion of the stored image data associated with a particular image. In some embodiments, a single similarity measure may be calculated between the compared image data and the entirety of the stored image data. For example, the similarity measure may be a maximum degree of similarity calculated between the captured image data and the stored data. Alternatively, the similarity measure may be average similarity between the captured image data and various portions of the stored image data. In embodiments in which comparing the captured image data to the stored image data includes performing a convolution resulting in a similarity matrix, portions of the similarity measure may be generated during comparison, and the similarity measure may be finalized to account for all comparison data once template-matching is complete.

Figure 10B:
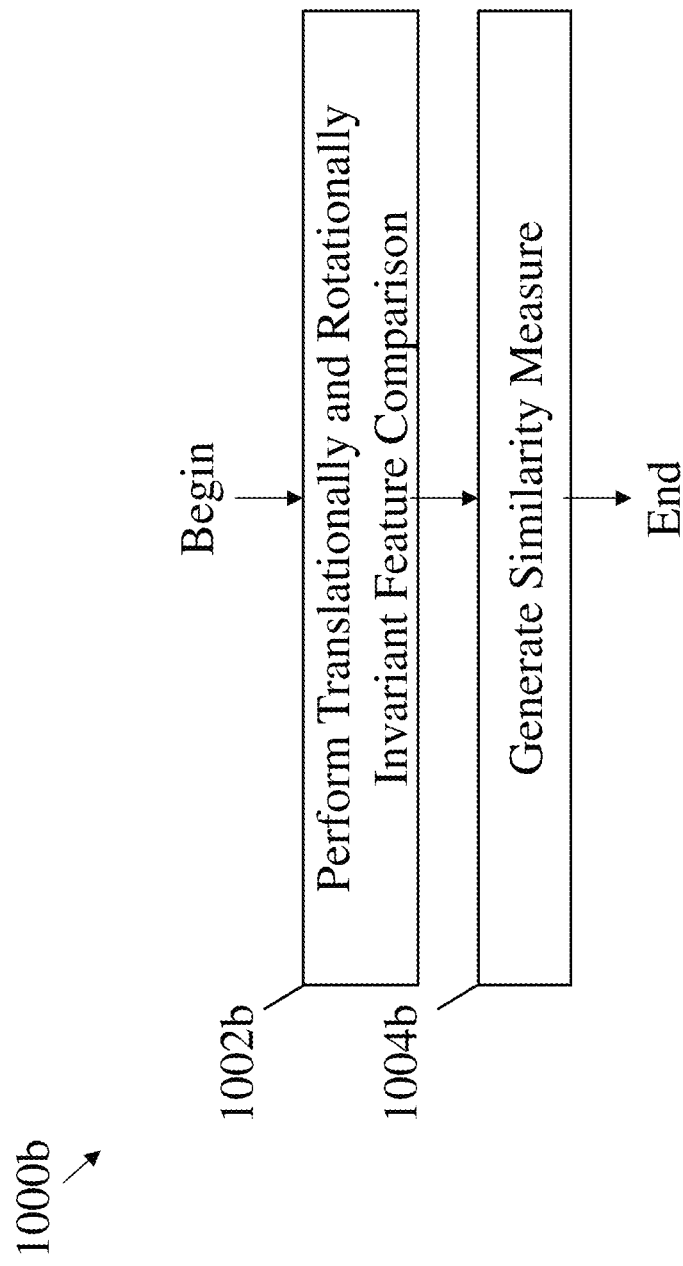
FIG. 10B is a flow diagram of a method for comparing translationally and rotationally invariant features of a person's retina fundus, in accordance with some embodiments of the method of FIG. 9.

FIG. 10B is a flow diagram of illustrative method 1000b for comparing translationally and rotationally invariant features indicated in the captured image data to those indicated in stored image data. For example, the translationally and rotationally invariant features may be indicated in the output of a TSC in accordance with the embodiments of FIGS. 5A-5C, 6, and 7-8. Method 1000b includes performing a translationally and rotationally invariant feature comparison at step 1002b, and generating a similarity measure at step 1004b. Method 1000b may be performed by device 120b or computer 140.

Performing the translationally and rotationally invariant feature comparison at step 1002b may include device 120b, computer 140 comparing relative positions and orientations of translationally and rotationally invariant features indicated in the captured image data to relative positions and orientations of translationally and rotationally invariant features indicated in the stored image data. For example, a SIFT or SURF comparison may be performed between some or all of the captured image data and the stored image data. In embodiments where the stored image data is associated with multiple images, separate comparisons may be performed for each portion of the stored image data associated with a particular image. Alternatively, in some embodiments, separate comparison may be performed for portions of the stored data indicating a particular retina fundus feature or group of features, for example including data associated with multiple images indicating the particular feature(s) in the multiple images. In some instances, the feature data may be combined from the multiple images and compared against the captured image data.

Generating a similarity measure at step 1004b may be conducted in the manner described for step 1004a in connection with FIG. 10A. For example, a similarity measure may be generated for each portion of the stored image data compared to the captured image data. Alternatively, a single similarity measure may be generated based on comparing portions of the stored image data associated with multiple images of a same person and/or focusing on different retina fundus features in each comparison, such that a similarity measure is generated for each image or for each particular feature or group of features.

III. Techniques for Accessing Electronic Records or Devices of a Person Based on a Retinal Image of the Person The inventors have developed techniques for securing and/or accessing electronic accounts or records or devices associated with a person with a biometric security system configured to enable access based on an image of the person's retina fundus. As one example, the inventors have developed techniques for securing a user account or a device using biometric identification. Further, the inventors have developed techniques for securing health information such as electronic health records associated with a person using biometric identification. Techniques for biometric identification may also be useful in other contexts of identifying a person, such as to secure a financial transaction. The biometric identification includes enabling access through identification of the person based on a retinal image and/or retinal measurement of the person. This retinal image and/or measurement of the person may be obtained through use of at least one of OCT and FLIO.

In some embodiments of FIGS. 1-2, device 120a or 120b may be configured to grant a person access to device 120a or 120b upon a successful identification. For example, device 120a may grant the person access upon receiving notification of a successful identification from computer 140. In some embodiments, device 120a may receive user account data specific to the person along with the notification. For example, device 120a may receive personalized settings from computer 140, such as a preferred audio/visual theme (e.g., a color theme and/or sounds), graphics settings (e.g., colorblind preferences), a personalized home screen (e.g., desktop background), and/or software applications previously accessed by the person for operating device 120a. In some embodiments, device 120b may have personalized settings stored on storage medium 126, and may select the personalized settings specific to the person upon successful identification. Alternatively or additionally, device 120a or device 120b may be configured to grant the person access to various other types of accounts such as a social media account on the internet, and/or a financial account for conducting a transaction.

In some embodiments of FIGS. 1-2, device 120a or 120b may be configured to provide access to health information such as electronic health records upon a successful identification. For example, computer 140 may store health information associated with one or more people, and upon successfully identifying a person, may transmit health information associated with the person to device 120a. Alternatively, device 120b may store the health information thereon, which may be obtained, for example from storage medium 126, upon successfully identifying the person. In some embodiments, device 120a or 120b, or computer 140 may update the health information based on retina fundus features indicated in the captured image(s). For example, in some embodiments, the health information may be updated to include the captured image(s) and/or feature data extracted therefrom during identification or otherwise. In this way, health information may be updated each time the person logs into device 120a or 120b. In some embodiments, the person may update electronic health records by reporting symptoms the person is experiencing directly into their electronic health records using device 120a or 120b rather than frequently having to meet in person with their healthcare professional.

Figure 11:
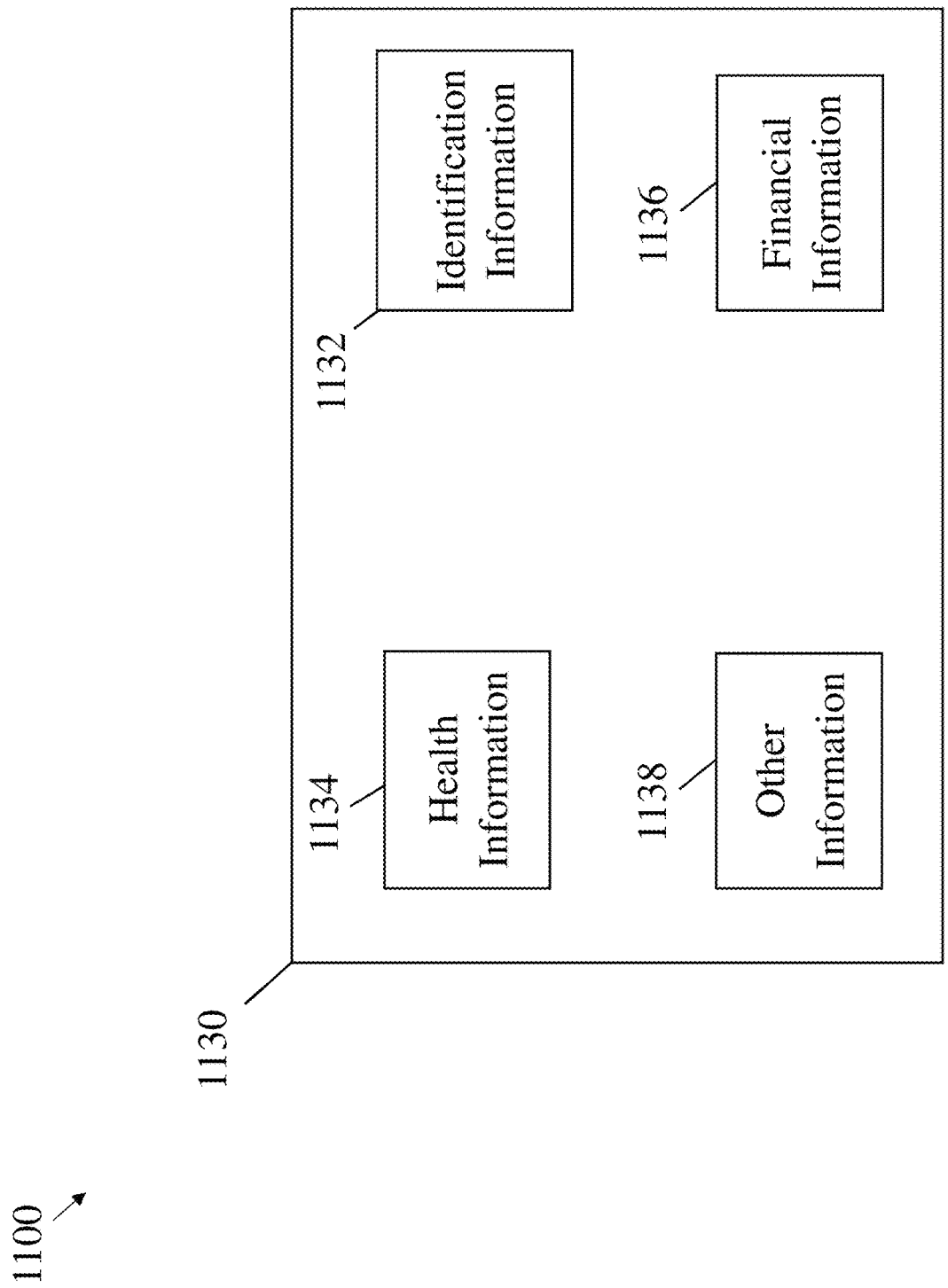
FIG. 11 is a block diagram illustrating an exemplary user interface in accordance with the embodiments of FIGS. 1-2.

FIG. 11 is a block diagram illustrating exemplary user interface 1100 in accordance with the embodiments of FIGS. 1-2. For example, user interface 1100 is provided on display 1130, which may be a display of device 120a or 120b.

Display 1130 may be a liquid crystal display (LCD) screen such as a computer monitor or phone screen, or alternatively may be a projection or hologram. In some embodiments, display 1130 may include a touchscreen configured for user interaction by pressing content which appears on the touchscreen. In some embodiments, display 1130 may be integrated with device 120a or 120b. Alternatively, in some embodiments, display 1130 may be separate from device 120a or 120b and may be coupled through a wired or wireless connection to device 120a or 120b.

Display 1130 includes portions for identification information 1132, health information 1134, financial information 1136, and other information 1138 on display 1130. In some embodiments, identification information 1132, health information 1134, and/or financial information 1136 may appear at edges of display 1130 while other information 1138 is presented to a user. As a non-limiting example, identification information 1132 may include a person's username, health information 1134 may include the person's stress level, financial information 1136 may include the person's bank account balance, and other information 1138 may include a message received over social media.

In some embodiments, identification information 1132 may indicate to a user whether an identification was successful. For example, identification information 1132 may include a notification indicating a successful identification. Alternatively or additionally, identification information 1132 may include the name of the identified person obtained using biometric identification.

In some embodiments, health information 1134, financial information, and/or other information 1138 may be obtained during or in addition to biometric identification. In some embodiments, device 120a or 120b may be configured to access and/or update health information associated with the person upon successful identification. Alternatively or additionally, device 120a or 120b may be configured to access and/or update financial or other account information associated with the person upon successful identification.

Health information 1134 may be obtained from computer 140 in accordance with the embodiment of FIG. 1 or from storage medium 126 of device 120b in accordance with the embodiment of FIG. 2. In some embodiments, health information 1134 may include a notification with a health warning, for example, based on information obtained from computer 140 or storage medium 126. Health information 1134 may include risk assessments associated with diabetes, cardiovascular disease, concussion, Parkinson's disease, Alzheimer's disease, and/or stress. In some embodiments, the health information may alternatively or additionally include risk assessments specific to the person's retina health. For example, the risk assessments may be associated with diabetic retinopathy, age-related macular degeneration, macular edema, retinal artery occlusion, retinal nerve-fiber layer, and/or glaucoma.

Financial information 1136 may be obtained from computer 140 in accordance with the embodiment of FIG. 1 or from storage medium 126 of device 120b in accordance with the embodiment of FIG. 2. In some embodiments, financial information 1136 may include balances for one or more financial accounts associated with the person such as banking or investment accounts.

It should be appreciated that display 1130 may include only some of identification information 1132, health information 1134, financial information 1136, and/or other information 1138, as this example merely demonstrates how a user may interact with multiple forms of information in accordance with various embodiments.

Patients typically access and/or update their electronic health records by consulting their healthcare professionals in person or through an online database accessible with a password or passcode. As described in section II, the inventors have recognized that biometric security systems configured to identify a person using a captured image of the person's retina fundus as described herein provide enhanced protection beyond passwords and passcodes while achieving lower false rejection and false acceptance rates than existing biometric security systems. Security and confidentiality of patients' health information is an important consideration when making patients' health information more accessible and easy for patients to update by themselves. If electronic health records are left unsecured or inadequately secured, parties other than patients and their healthcare professionals may be able to access sensitive health information. The resulting lack of confidentiality may cause patients to lose trust that their information is private, and may be further dissuaded from seeking medical attention. In addition, if patients' electronic health records could be forged or otherwise fraudulently altered, healthcare professionals would not be able to make proper diagnoses. Accordingly, the inventors have developed systems for accessing health information securely using biometric identification systems, such that health information may be more accessible to patients while maintaining confidentiality and security.

In some embodiments, device 120a or device 120b may be configured to identify a person and access the person's electronic health records, even if the person is unconscious. For example, during a mass casualty event such as a natural disaster, unconscious victims may be identified and their electronic health records may be obtained using device 120a or device 120b. For example, a first responder such as an Emergency Medical Technician (EMT) may use the device to identify each person and to access health information using the device in order to more accurately conduct triage. Thus, the device may facilitate responding to events such as natural disasters in a quick and organized fashion.

Figure 12:
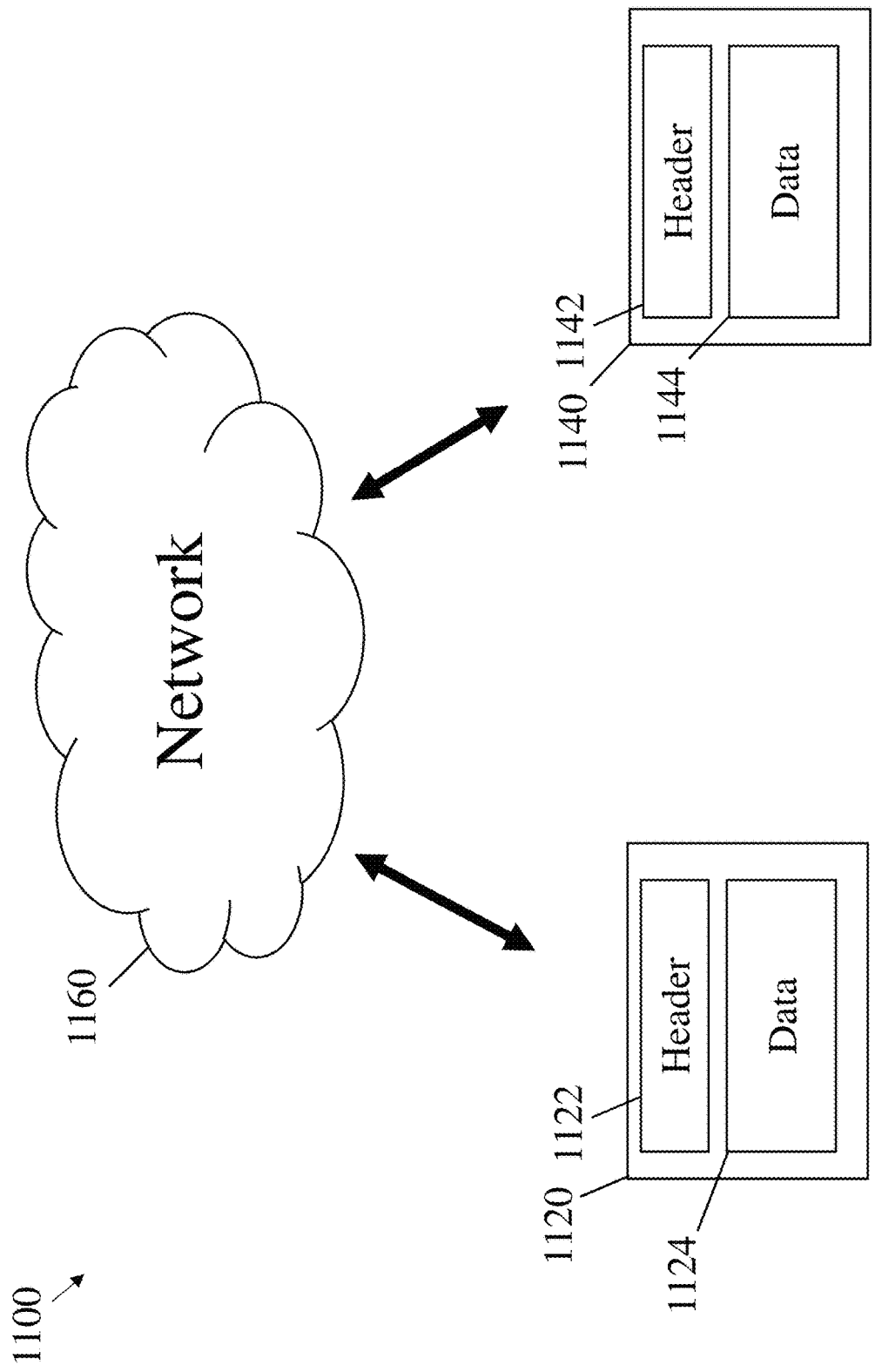
FIG. 12 is a block diagram illustrating an exemplary distributed ledger, components of which are accessible over a network, in accordance with some embodiments of the technology described herein.

Referring to FIG. 12, health or other account information may be stored on one or more components of a distributed ledger such as a blockchain. The inventors have recognized that a distributed ledger offers a concrete record of changes made to data stored on the ledger. For example, each component of the ledger may have a unique identifier which is updated to reflect a time and/or scope of changes made to the component, and/or changes made to other components within the ledger. Accordingly, a distributed ledger may facilitate detecting whether information stored on the ledger, such as identification information, user account data, financial data, or health information, has been changed, as well as when and to what extent changes were made. The inventors have recognized that securing access to components of a distributed ledger for electronic health records with a biometric identification system enhances the accuracy and confidentiality of the electronic health records. In some embodiments, changes to health information stored on the distributed ledger may only be made by the person with whom the health information is associated, or an authorized healthcare professional such as the person's doctor.

In accordance with various embodiments, components of a distributed ledger may include user account data, financial data, health information such as electronic health records, stored image data and/or identification information associated with the person or others.

FIG. 12 is a block diagram illustrating exemplary distributed ledger 1200 including components 1220 and 1240 accessible over network 1260. Distributed ledger 1200 may implement a distributed data structure with component(s) 1220 and 1240 of the ledger being stored on various devices and computers such as device 120a, device 120b, or computer 140, and accessible over communication network 160. For example, in some embodiments, network 1260 may be communication network 160 of FIG. 1, such that components 1220 and 1240 may be stored on or may be accessible to device 120a and/or computer 140. Alternatively, network 1260 may be a sub-network of communication network 160, such as a peer-to-peer (P2P) network distributed across communication network 160 but not accessible to all devices on communication network 160. According to a non-limiting example, distributed ledger 1200 may implement a blockchain, with components 1220 and 1240 serving as blocks with block headers linked to other blocks in the chain.

Component 1220 includes header 1222 and data 1224, and component 1240 includes header 1242 and data 1244. In accordance with various embodiments, data 1224 and/or 1244 may include stored image data, health information such as electronic health records, user account data, financial data, and/or identification information associated with a person. Headers 1222 and 1242 may each include a unique identifier specific to component 1220 and 1240, such as an address or hash for identifying component 1220 or 1240. The identifier may include information referring back and/or forward to one or more other components in the chain. For example, if component 1220 and 1240 are linked, header 1222 may include information referring to component 1240, and/or header 1242 may include information referring to component 1220. Alternatively or additionally, the identifier may include information based on changes made to data 1224 or 1244 of each component, such as the time or extent to which the changes were made. In some embodiments, the identifier may result from a mathematical operation involving identifiers of other components and/or information associated with changes to the data of the component. For example, data 1224 of component 1220 may include a person's identification information and/or electronic health records, which may be changed to include updated health information. Accordingly, header 1222 may be updated to indicate that changes were made, and in some cases, the scope of the changes. In addition, headers of other components linked to component 1220 may also be updated to include the updated identifier of the component 1220. For example, in some embodiments where component 1240 is linked to component 1220, header 1242 may be updated based on changes to header 1222 and/or vice versa.

In the embodiments of FIGS. 1-2, device 120*a* and/or computer 140 may, at times, store one or more components of the distributed ledger. Alternatively or additionally, device 120*a* and/or computer 140 may be configured to access component(s) 1220 and/or 1240 of distributed ledger 1200 having data 1224 and/or 1244 associated with the person.

In the embodiments of FIGS. 1-10B, biometric identification may be performed using stored image data from components 1220 and/or 1240 of distributed ledger 1200. For example, device 120*b* or computer 140 may obtain the stored image data from component(s) 1220 and/or 1240 of distributed ledger 1200. Further, identification information may be stored as at least a portion of data 1224 and/or 1244 of components 1220 and/or 1240. In some embodiments, data 1224 of component 1220 may include stored image data, as well as a link to component 1240 which may store identification information associated with the stored image data in data 1244. Upon determining that stored image data on component 1220 has at least the predetermined degree of similarity to the captured image data, identification information associated with the person may be obtained from component 1220 having the stored image data, or may be obtained from linked component 1240.

IV. Techniques for Determining a Health Status of a Person Based on a Retinal Image of the Person The inventors have developed techniques for using a captured image of a person's retina fundus to determine the person's predisposition to certain diseases. For example, the appearance the person's retina fundus may indicate whether the person is at risk for various conditions such as diabetes, an adverse cardiovascular event, or stress, as described herein. As an advantage of integrating health status determination into a system for biometric identification, captured image data for identifying the person may be used to determine the person's health status. In accordance with various embodiments, the determination of the person's predisposition based on images of the person's retina fundus may be performed before, during, or after identifying the person. For example, the determination may be performed separately from the identification, or may be performed as an additional or alternative step during the identification.

The inventors have recognized that various medical conditions may be indicated by the appearance of a person's retina fundus. For example, diabetic retinopathy may be indicated by tiny bulges or micro-aneurysms protruding from the vessel walls of the smaller blood vessels, sometimes leaking fluid and blood into the retina. In addition, larger retinal vessels can begin to dilate and become irregular in diameter. Nerve fibers in the retina may begin to swell. Sometimes, the central part of the retina (macula) begins to swell, such as macular edema. Damaged blood vessels may close off, causing the growth of new, abnormal blood vessels in the retina. Glaucomatous optic neuropathy, or Glaucoma, may be indicated by thinning of the parapapillary retinal nerve fiber layer (RNFL) and optic disc cupping as a result of axonal and secondary retinal ganglion cell loss. The inventors have recognized that RNFL defects, for example indicated by OCT, are one of the earliest signs of glaucoma.

In addition, age-related macular degeneration (AMD) may be indicated by the macula peeling and/or lifting, disturbances of macular pigmentation such as yellowish material under the pigment epithelial layer in the central retinal zone, and/or drusen such as macular drusen, peripheral drusen, and/or granular pattern drusen. AMD may also be indicated by geographic atrophy, such as a sharply delineated round area of hyperpigmentation, nummular atrophy, and/or subretinal fluid. Stargardt's disease may be indicated by death of photoreceptor cells in the central portion of the retina. Macular edema may be indicated by a trench in an area surrounding the fovea. A macular hole may be indicated by a hole in the macula. Eye floaters may be indicated by non-focused optical path obscuring. Retinal detachment may be indicated by severe optic disc disruption, and/or separation from the underlying pigment epithelium. Retinal degeneration may be indicated by the deterioration of the retina. Central serous retinopathy (CSR) may be indicated by an elevation of sensory retina in the macula, and/or localized detachment from the pigment epithelium. Choroidal melanoma may be indicated by a malignant tumor derived from pigment cells initiated in the choroid. Cataracts may be indicated by opaque lens, and may also cause blurring fluorescence lifetimes and/or 2D retina fundus images. Macular telangiectasia may be indicated by a ring of fluorescence lifetimes increasing dramatically for the macula, and by smaller blood vessels degrading in and around the fovea. Alzheimer's disease and Parkinson's disease may be indicated by thinning of the RNFL. It should be appreciated that diabetic retinopathy, glaucoma, and other such conditions may lead to blindness or severe visual impairment if not properly screened and treated.

Accordingly, in some embodiments, systems and devices described herein may be configured to determine the person's predisposition to various medical conditions based on one or more images of the person's retina fundus. For example, if one or more of the above described signs of a particular medical condition (e.g., macula peeling and/or lifting for age-related macular degeneration) is detected in the image(s), the system and/or device may determine that the person is predisposed to that medical condition. In such situations, the system or device may notify the person directly and/or may notify the person's health professional of the person's predisposition.

Furthermore, in some embodiments, systems and devices described herein may make such medical predisposition determinations based on captured and stored images. For example, some signs such as thinning of the RNFL may be indicated by comparison of the captured image(s) to the stored images when identifying the person. While such a progression would pose a challenge for existing identification systems as it may result in a false rejection of the correct person, systems described herein may be configured to account for such differences upon determination of the person's medical condition. Thus, the inventors have developed systems and devices which not only detect signs of and determine a person's medical condition, but also adapt to account for the medical condition during identification.

Alternatively or additionally, in some embodiments, systems and devices described herein may make such medical predisposition determinations based on one or more outputs from a TSC. For example, one or more images of a person's retina fundus may be provided as an input to the TSC, which may provide one or more outputs indicative of features of the person's retina fundus. In some embodiments, each output may indicate a likelihood of a sign of a medical condition being in a particular portion of a particular image.

Alternatively, one or more outputs may indicate a likelihood of a sign of multiple medical conditions in a single or multiple images. Further, the output(s) may indicate the likelihood of multiple signs of one or of multiple medical conditions in a single or multiple images. The output(s) may indicate the likelihood of one or more signs of one or more medical conditions being present across multiple locations in a single or in multiple images. Accordingly, a determination of the person's predisposition to various medical conditions may be made based on the output(s) from the TSC. When stored image data is also provided as input to the TSC, the output(s) from the TSC may not only be used to identify the person as described herein, but also to make medical condition determinations based on the features indicated in the output(s).

In some embodiments, upon a successful identification, risk assessments in the person's health information may be updated based on the appearance of retina fundus features in the captured image data. For example, in accordance with the embodiment of FIG. 1, the risk assessments may be updated on computer 140 and/or may be provided to device 120a for display in user interface 1100 of FIG. 11. In accordance with the embodiment of FIG. 2, the risk assessments may be updated on device 120b and/or may be provided for display in user interface 1100.

V. Techniques for Diagnosing a Health Condition of a Person Based on a Retinal Image of the Person The inventors have also developed techniques for using a captured image of a person's retina fundus to diagnose various health conditions or diseases of the person. For example, in some embodiments, any of the health conditions described in section IV may be diagnosed before identification, during identification, after a successful identification, and/or using data accumulated during one or more identifications. Alternatively or additionally, such conditions may include retinoblastoma, or correctable vision problems such as nearsightedness or amblyopia. Such determinations may be performed in the manner described in section IV. In accordance with the embodiment of FIG. 1, computer 140 may perform the diagnosis and provide the results of the diagnosis to device 120a. In accordance with the embodiment of FIG. 2, device 120b may perform the diagnosis and provide the results of the diagnosis thereon. In some embodiments, the results of the diagnosis may be alternatively or additionally provided to a healthcare professional, such as the person's doctor.

VI. Applications

As described, a captured image of a person's retina fundus can be used to identify the person, access an electronic record or secure device of the person, determine a health status of the person (including determining the person's propensity to obtaining certain diseases or conditions), and/or diagnose an actual disease or health condition (such as Alzheimer's, diabetes, certain autoimmune disorders, etc.) of the person. In addition, systems and devices described herein may be configured to determine a person's vital signs, blood pressure, heart rate, and/or red and white blood cell counts. Further, systems and devices described herein may be configured for use with other medical devices such as ultrasound probes, magnetic resonance imaging (MRI) systems, or others. Examples of ultrasound probes for use with systems and devices as described herein are described in U.S. Pat. Application No. 2017/0360397, titled "UNIVERSAL ULTRASOUND DEVICE AND RELATED APPARATUS AND METHODS", which is herein incorporated by reference in its entirety. Examples of MRI systems for use with systems and devices as described herein are described in U.S. Pat. Application No. 2018/0164390, titled "ELECTROMAGNETIC SHIELDING FOR MAGNETIC RESONANCE IMAGING METHODS AND APPARATUS", which is herein incorporated by reference in its entirety.

Having thus described several aspects and embodiments of the technology set forth in the disclosure, it is to be appreciated that various alterations, modifications, and improvements will readily occur to those skilled in the art. Such alterations, modifications, and improvements are intended to be within the spirit and scope of the technology described herein. For example, those of ordinary skill in the art will readily envision a variety of other means and/or structures for performing the function and/or obtaining the results and/or one or more of the advantages described herein, and each of such variations and/or modifications is deemed to be within the scope of the embodiments described herein. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, inventive embodiments may be practiced otherwise than as specifically described. In addition, any combination of two or more features, systems, articles, materials, kits, and/or methods described herein, if such features, systems, articles, materials, kits, and/or methods are not mutually inconsistent, is included within the scope of the present disclosure.

The above-described embodiments can be implemented in any of numerous ways. One or more aspects and embodiments of the present disclosure involving the performance of processes or methods may utilize program instructions executable by a device (e.g., a computer, a processor, or other device) to perform, or control performance of, the processes or methods. In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other tangible computer storage medium) encoded with one or more programs that, when executed on one or more computers or other processors, perform methods that implement one or more of the various embodiments described above. The computer readable medium or media can be transportable, such that the program or programs stored thereon can be loaded onto one or more different computers or other processors to implement various ones of the aspects described above. In some embodiments, computer readable media may be non-transitory media.

The terms "program" or "software" are used herein in a generic sense to refer to any type of computer code or set of computer-executable instructions that can be employed to program a computer or other processor to implement various aspects as described above. Additionally, it should be appreciated that according to one aspect, one or more computer programs that when executed perform methods of the present disclosure need not reside on a single computer or processor, but may be distributed in a modular fashion among a number of different computers or processors to implement various aspects of the present disclosure.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer, as non-limiting examples. Additionally, a computer may be embedded in a device not generally regarded as a computer but with suitable processing capabilities, including a Personal Digital Assistant (PDA), a smartphone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible formats.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

Also, as described, some aspects may be embodied as one or more methods. In some embodiments, methods may incorporate aspects of one or more techniques described herein.

Figure 13A:
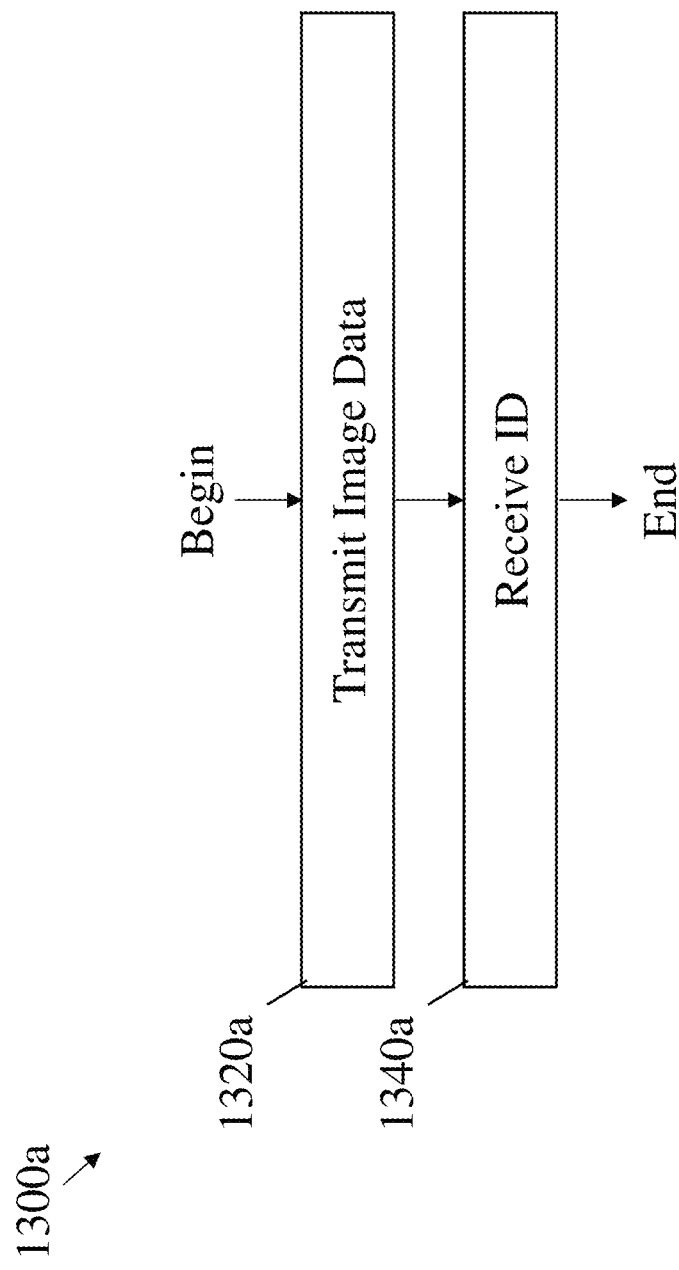
FIG. 13A is a flow diagram illustrating an exemplary method including transmitting, over a communication network, first image data associated with and/or including a first image of a person's retina fundus, and receiving, over the communication network, an identity of the person, in accordance with some embodiments of the technology described herein.

For example, FIG. 13A is a flow diagram illustrating exemplary method 1300a including transmitting, over a communication network [e.g., to the cloud], first image data associated with and/or including a first image of a person's retina fundus at step 1320a, and receiving, over the communication network, an identity of the person at step 1340a, in accordance with some or all of the embodiments described herein.

Figure 13B:
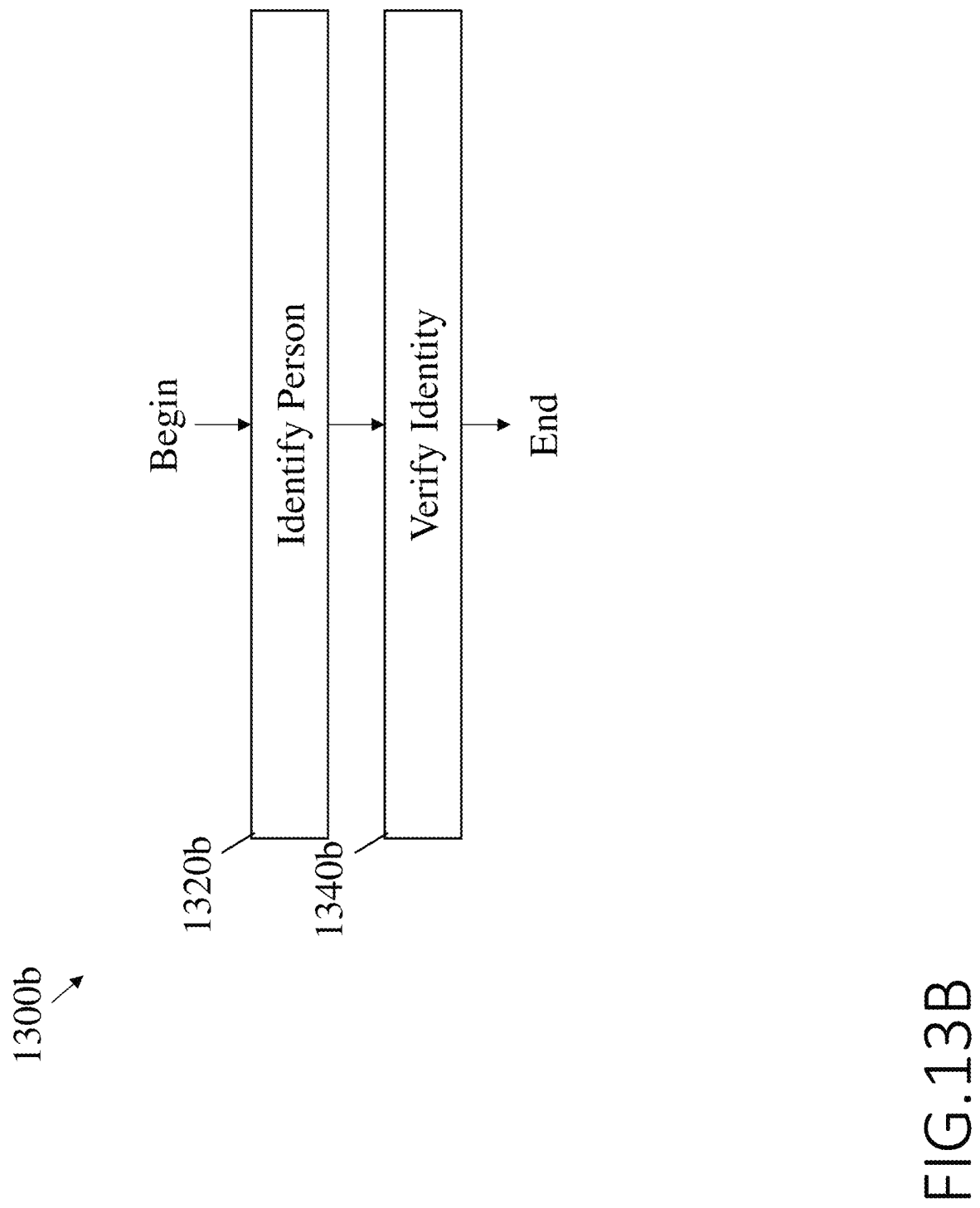
FIG. 13B is a flow diagram illustrating an exemplary method including, based on first image data associated with and/or including a first image of a person's retina fundus, identifying the person, and, based on a first biometric characteristic of the person, verifying an identity of the person, in accordance with some embodiments of the technology described herein.

FIG. 13B is a flow diagram illustrating exemplary method 1300b including, based on first image data associated with and/or including a first image of a person's retina fundus, identifying the person at step 1320b, and, based on a first biometric characteristic of the person, verifying an identity of the person at step 1340b, in accordance with some or all of the embodiments described herein. It should be appreciated that, in some embodiments, step 1320a may alternatively or additionally include identifying the person based on a first of multiple types of features indicated in the first image data, and/or 1340b may include verifying the identity based on a second of the multiple types of features.

Figure 13C:
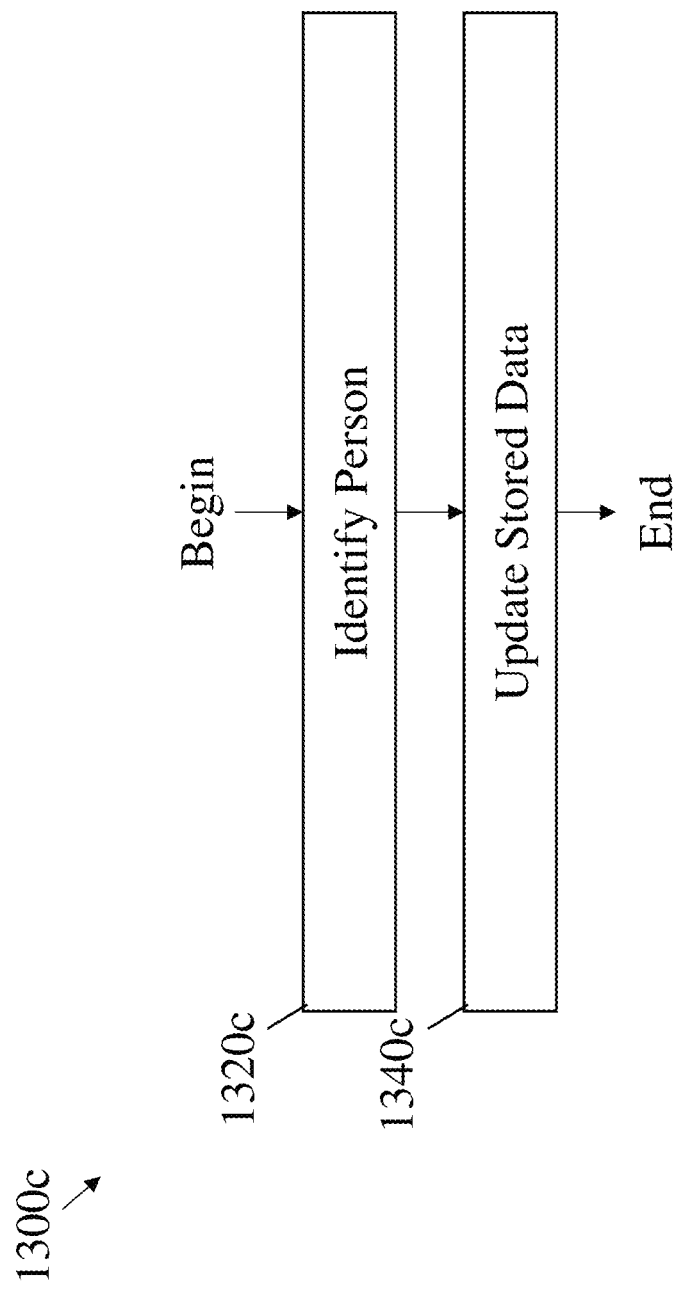
FIG. 13C is a flow diagram illustrating an exemplary method including, based on first image data associated with and/or including a first image of a person's retina fundus, identifying the person and updating stored data associated with a plurality of retina fundus images, in accordance with some embodiments of the technology described herein.

FIG. 13C is a flow diagram illustrating exemplary method 1300c including, based on first image data associated with and/or including a first image of a person's retina fundus, identifying the person at step 1320c and updating stored data associated with a plurality of retina fundus images at step 1340c, in accordance with some or all embodiments described herein.

Figure 13D:
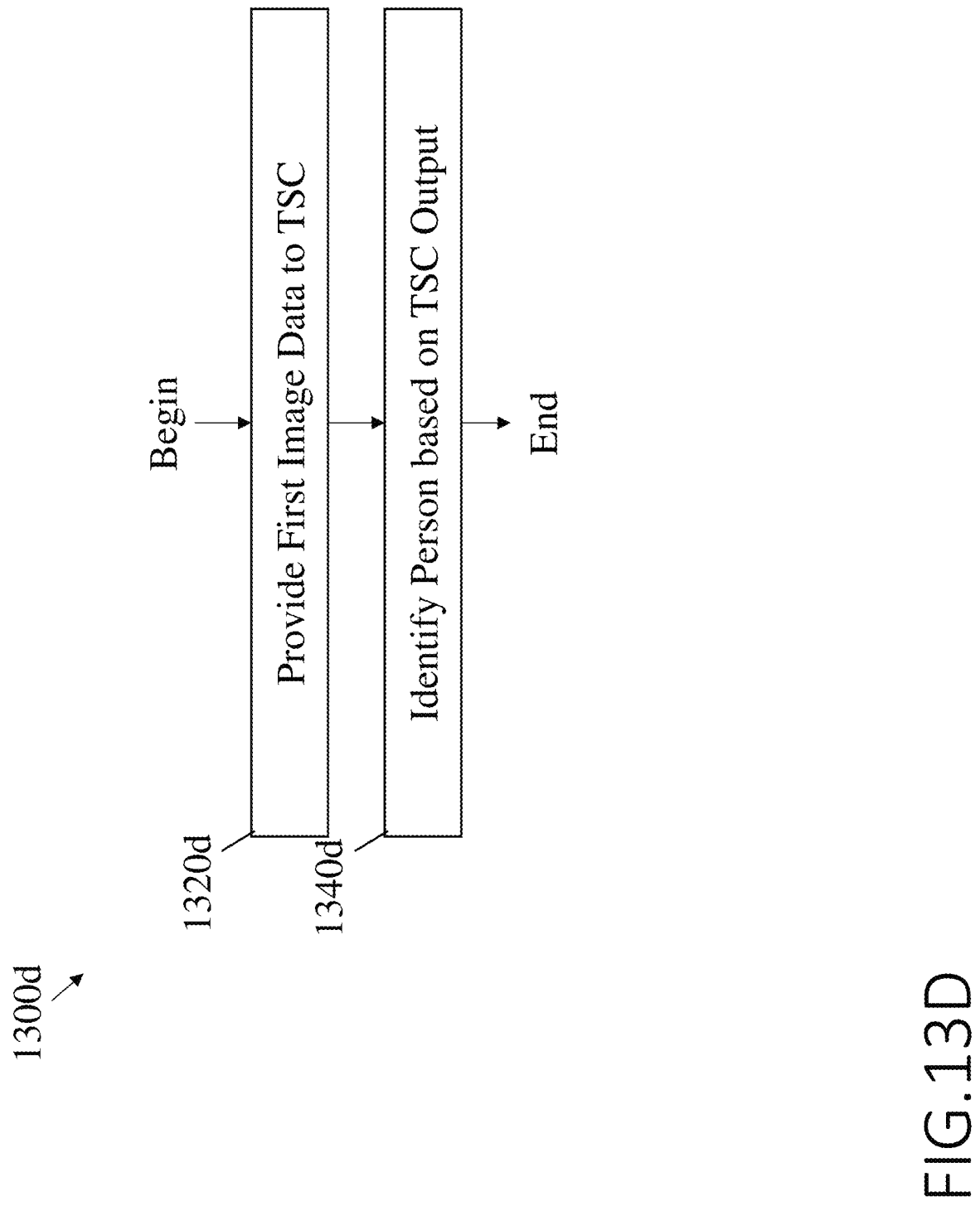
FIG. 13D is a flow diagram illustrating an exemplary method including providing, as a first input to a trained statistical classifier (TSC), first image data associated with and/or including a first image of a person's retina fundus, and, based on at least one output from the TSC, identifying the person, in accordance with some embodiments of the technology described herein.

FIG. 13D is a flow diagram illustrating exemplary method 1300d including providing, as a first input to a trained statistical classifier (TSC), first image data associated with and/or including a first image of a person's retina fundus at step 1320d and, based on at least one output from the TSC, identifying the person at step 1340d, in accordance with some or all embodiments described herein.

Figure 13E:
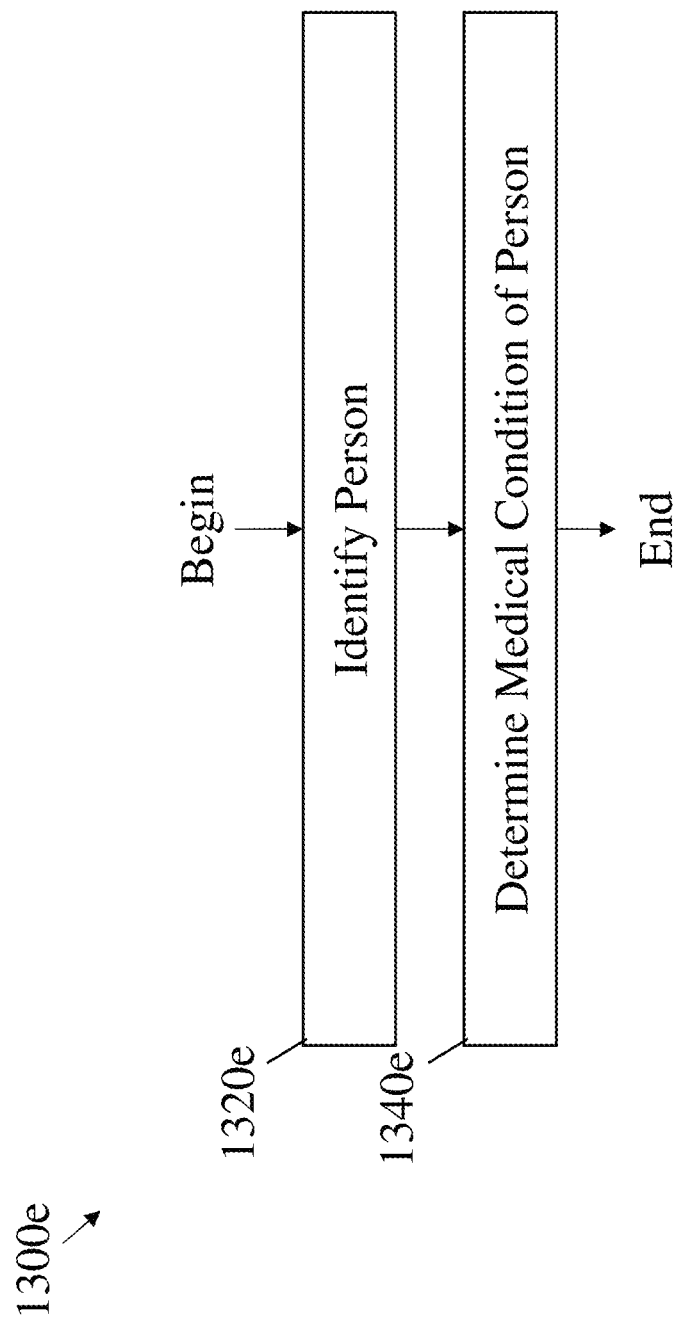
FIG. 13E is a flow diagram illustrating an exemplary method including, based on first image data associated with and/or including a first image of a person's retina fundus, identifying the person, and determining a medical condition of the person, in accordance with some embodiments of the technology described herein.

FIG. 13E is a flow diagram illustrating exemplary method 1300e including, based on first image data associated with and/or including a first image of a person's retina fundus, identifying the person at step 1320e and determining a medical condition of the person at step 1340e, in accordance with some or all embodiments described herein.

Figure 13F:
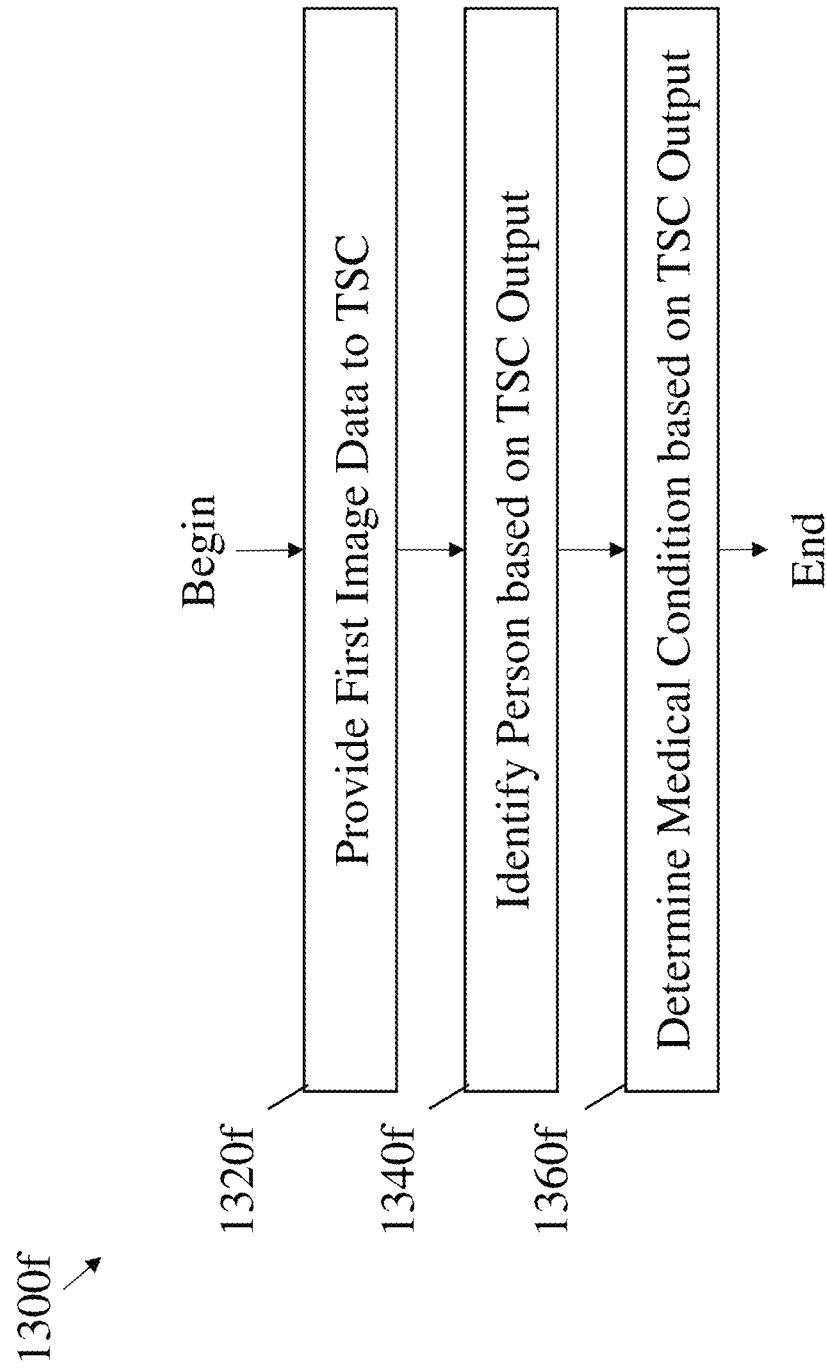
FIG. 13F is a flow diagram illustrating an exemplary method including providing, as a first input to a trained statistical classifier (TSC), first image data associated with and/or including a first image of a person's retina fundus, based on at least one output from the TSC, identifying the person at step, and determining a medical condition of the person, in accordance with some embodiments of the technology described herein.

FIG. 13F is a flow diagram illustrating exemplary method 1300g including providing, as a first input to a trained statistical classifier (TSC), first image data associated with and/or including a first image of a person's retina fundus at step 1320f, based on at least one output from the TSC, identifying the person at step 1340f, and determining a medical condition of the person at step 1360f, in accordance with some or all embodiments described herein.

The acts performed as part of the methods may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

What is claimed is:

1. A method comprising:
   using an imaging and/or measurement apparatus to perform:
      transmitting, over a communication network, first image data or first measurement data, the first image data being associated with or including a first image of a person's retina fundus, and the first measurement data being associated with or including a first measurement of the person's retina fundus; and
      receiving, from a computer, and over the communication network, an identity of the person, wherein the computer is configured to determine the identity of the person based on the first image data or the first measurement data.

2. The method of claim 1, further comprising obtaining, from the imaging and/or measurement apparatus, the first image and/or the first measurement.

3. The method of claim 2, further comprising capturing, by the imaging and/or measurement apparatus, the first image and/or the first measurement of the person's retina fundus.

4. The method of claim 1, wherein transmitting the first image data comprises transmitting a compressed version of the first image, and wherein transmitting the first measurement data comprises transmitting a compressed version of the first measurement.

5. The method of claim 1, further comprising extracting the first image data from the first image and/or extracting the first measurement data from the first measurement, wherein the first image data and/or the first measurement data is indicative of features of the person's retina fundus.

6. The method of claim 1, wherein the first image data and/or the first measurement data comprises translationally and rotationally invariant features of the person's retina fundus.

7. The method of claim 6, wherein the translationally and rotationally invariant features comprise branch endings and bifurcations of blood vessels of the person's retina fundus.

8. The method of claim 6, wherein the translationally and rotationally invariant features comprise an optic disc of the person's retina fundus.

9. The method of claim 1, wherein the imaging and/or measurement apparatus is configured for widefield imaging and/or measurement.

10. The method of claim 1, wherein the imaging and/or measurement apparatus comprises a digital camera integrated in a mobile phone.

11. The method of claim 1, further comprising encrypting the first image data and/or the first measurement data before transmitting, over the communication network, the first image data and/or the first measurement data.

12. The method of claim 1, further comprising granting the person access to a device after receiving the identity.

13. The method of claim 1, further comprising transmitting, over the communication network, the first image data and the first measurement data.

14. The method of claim 1, wherein the first image data is associated with and includes the first image of the person's retina fundus, and wherein the first measurement data is associated with and includes the first measurement of the person's retina fundus.

* * * * *